US007858745B2

(12) United States Patent
Lavie et al.

(10) Patent No.: US 7,858,745 B2
(45) Date of Patent: Dec. 28, 2010

(54) USE OF SPECIFICALLY ENGINEERED ENZYMES TO ENHANCE THE EFFICACY OF PRODRUGS

(75) Inventors: Arnon Lavie, Chicago, IL (US); Manfred Konrad, Goettingen (DE); Farhad Ravandi, Houston, TX (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 432 days.

(21) Appl. No.: 11/760,399

(22) Filed: Jun. 8, 2007

(65) Prior Publication Data

US 2007/0258968 A1 Nov. 8, 2007

Related U.S. Application Data

(63) Continuation of application No. 10/791,155, filed on Mar. 1, 2004, now Pat. No. 7,419,811.

(60) Provisional application No. 60/451,207, filed on Feb. 28, 2003, provisional application No. 60/471,660, filed on May 19, 2003, provisional application No. 60/541,496, filed on Feb. 3, 2004.

(51) Int. Cl.
*C07K 14/00* (2006.01)
*C12N 15/00* (2006.01)
(52) U.S. Cl. ............... 530/350; 514/2; 435/68.1
(58) Field of Classification Search ............ None
See application file for complete search history.

(56) References Cited

U.S. PATENT DOCUMENTS

| 5,914,258 | A | * | 6/1999 | Wei et al. ............... 435/194 |
| 6,299,876 | B1 | | 10/2001 | Bagshawe |
| 2001/0012835 | A1 | | 8/2001 | Fine |
| 2007/0037269 | A1 | * | 2/2007 | Marliere et al. ......... 435/183 |

FOREIGN PATENT DOCUMENTS

| FR | 2823219 | * | 10/2002 |
| WO | WO 01/88106 | | 5/2001 |
| WO | WO 02/083892 | | 10/2002 |

OTHER PUBLICATIONS

Johansson et al, Nature Structural Biology, 8: 616-619, 2001.*
Sequence search result-SEQ ID No. 1 (2009).*
Bergman et al., 1999, Biochem. Pharmacol. 57: 397-406.
Blackstock et al., 2001, Clin. Cancer Res. 7:3263-8.
Blakey et al., 1997, Exp. Opin. Ther. Patents, 7:966-977.
Estey et al., 1987, Leukemia 1:580-3.
Estey, 2000, Blood 96: 1670-3.
Gandhi et al., 1993, J. Clin. Oncol. 11: 116-24.
Gladstone et al., 2003, Blood, 102: 138(A).
Goan et al., 1999, Cancer Res. 59: 4204-7.
Hapke et al., 1996, Cancer Res. 56: 2343-7.
Hubert et al., 1999, Proc Natl Acad Sci USA 7:4523-8.
Iacoboni et al., 1986, J. Clin. Oncol. 4:1079-88.
Kabouridis, 2003, Trends in Biotechnology 21:498-503.
Kakihara et al., 1998, Leuk. Lymphoma 31:405-9.
Kantarjian et al., 1986, Am. J. Med. 81:387-94.
Kossman et al., 1999, Clin. Can. Res. 5:2748-55.
Knecht et al., 2002, EMBO J. 21:1873-1880.
Lotfi et al., 1999, Clin. Cancer Res. 5:2438-44.
Mansson et al., 2003, Biochem. Pharmacol. 65:237-247.
Owens et al., 1992, Cancer Res. 52:2389-93.
Plunkett et al., 1985, Semin Oncol 12:20-30.
Ruiz van Haperen et al., 1994, Cancer Res. 54: 4138-43.
Sandlie and Brekke 2003, Nat. Rev. Drug Discovery 2:52-62.
Stegmann et al., 1995, Blood 85: 1188-94.
Van Rompay, et al., 2000, Pharmacol. Ther. 87: 189-98.
Zhu et al., 2000, J. Biol. Chem. 275: 26727.
Iyidogan, Pinar, et al., "Systematic Exploration of Active Site Mutations on Human Deoxycytidine Kinase Substrate Specificity," Biochemistry, 2008, vol. 47, pp. 4711-4720.

* cited by examiner

*Primary Examiner*—Larry R. Helms
*Assistant Examiner*—Lei Yao
(74) *Attorney, Agent, or Firm*—McDonnell Boehnen Hulbert & Berghoff LLP

(57) ABSTRACT

The invention provides methods for enhancing efficiency of prodrugs by specifically engineered enzymes with enhanced activity towards nucleoside analogs used in cancer chemotherapy, and delivering the enzymes to specific target cells in a patient. The invention also provides modified deoxycytidine kinase (dCK) mutants with such enhanced activity. Furthermore, the invention provides antibody-conjugated enzymes that can be specifically delivered to leukemic blast cells in vivo or ex vivo.

9 Claims, 9 Drawing Sheets

SEQUENCE LISTING

```
<160> NUMBER OF SEQ ID NOS: 6

<210> SEQ ID NO 1
<211> LENGTH: 260
<212> TYPE: PRT
<213> ORGANISM: Homo sapiens

<400> SEQUENCE: 1

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
            20                  25                  30

Gly Lys Ser Thr Phe Val Asn Ile Leu Lys Gln Leu Cys Glu Asp Trp
        35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
```

```
            115                 120                 125
Ser Val Tyr Ser Asp Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
        260

<210> SEQ ID NO 2
<211> LENGTH: 277
<212> TYPE: PRT
<213> ORGANISM: Homo sapiens

<400> SEQUENCE: 2

Met Ala Ala Gly Arg Leu Phe Leu Ser Arg Leu Arg Ala Pro Phe Ser
1               5                   10                  15

Ser Met Ala Lys Ser Pro Leu Glu Gly Val Ser Ser Arg Gly Leu
            20                  25                  30

His Ala Gly Arg Gly Pro Arg Arg Leu Ser Ile Glu Gly Asn Ile Ala
        35                  40                  45

Val Gly Lys Ser Thr Phe Val Lys Leu Leu Thr Lys Thr Tyr Pro Glu
    50                  55                  60

Trp His Val Ala Thr Glu Pro Val Ala Thr Trp Gln Asn Ile Gln Ala
65                  70                  75                  80

Ala Gly Asn Gln Lys Ala Cys Thr Ala Gln Ser Leu Gly Asn Leu Leu
                85                  90                  95

Asp Met Met Tyr Arg Glu Pro Ala Arg Trp Ser Tyr Thr Phe Gln Thr
            100                 105                 110

Phe Ser Phe Leu Ser Arg Leu Lys Val Gln Leu Glu Pro Phe Pro Glu
        115                 120                 125

Lys Leu Leu Gln Ala Arg Lys Pro Val Gln Ile Phe Glu Arg Ser Val
    130                 135                 140

Tyr Ser Asp Arg Tyr Ile Phe Ala Lys Asn Leu Phe Glu Asn Gly Ser
145                 150                 155                 160

Leu Ser Asp Ile Glu Trp His Ile Tyr Gln Asp Trp His Ser Phe Leu
                165                 170                 175

Leu Trp Glu Phe Ala Ser Arg Ile Thr Leu His Gly Phe Ile Tyr Leu
            180                 185                 190

Gln Ala Ser Pro Gln Val Cys Leu Lys Arg Leu Tyr Gln Arg Ala Arg
        195                 200                 205

Glu Glu Glu Lys Gly Ile Glu Leu Ala Tyr Leu Glu Gln Leu His Gly
    210                 215                 220
```

```
Gln His Glu Ala Trp Leu Ile His Lys Thr Thr Lys Leu His Phe Glu
225                 230                 235                 240

Ala Leu Met Asn Ile Pro Val Leu Val Leu Asp Val Asn Asp Asp Phe
                245                 250                 255

Ser Glu Glu Val Thr Lys Gln Glu Asp Leu Met Arg Glu Val Asn Thr
            260                 265                 270

Phe Val Lys Asn Leu
            275

<210> SEQ ID NO 3
<211> LENGTH: 250
<212> TYPE: PRT
<213> ORGANISM: Drosophila

<400> SEQUENCE: 3

Met Ala Glu Ala Ala Ser Cys Ala Arg Lys Gly Thr Lys Tyr Ala Glu
1               5                   10                  15

Gly Thr Gln Pro Phe Thr Val Leu Ile Glu Gly Asn Ile Gly Ser Gly
                20                  25                  30

Lys Thr Thr Tyr Leu Asn His Phe Glu Lys Tyr Lys Asn Asp Ile Cys
            35                  40                  45

Leu Leu Thr Glu Pro Val Glu Lys Trp Arg Asn Val Asn Gly Val Asn
50                  55                  60

Leu Leu Glu Leu Met Tyr Lys Asp Pro Lys Lys Trp Ala Met Pro Phe
65                  70                  75                  80

Gln Ser Tyr Val Thr Leu Thr Met Leu Gln Ser His Thr Ala Pro Thr
                85                  90                  95

Asn Lys Lys Leu Lys Ile Met Glu Arg Ser Ile Phe Ser Ala Arg Tyr
            100                 105                 110

Cys Phe Val Glu Asn Met Arg Arg Asn Gly Ser Leu Glu Gln Gly Met
        115                 120                 125

Tyr Asn Thr Leu Glu Glu Trp Tyr Lys Phe Ile Glu Glu Ser Ile His
130                 135                 140

Val Gln Ala Asp Leu Ile Ile Tyr Leu Arg Thr Ser Pro Glu Val Ala
145                 150                 155                 160

Tyr Glu Arg Ile Arg Gln Arg Ala Arg Ser Glu Glu Ser Cys Val Pro
                165                 170                 175

Leu Lys Tyr Leu Gln Glu Leu His Glu Leu His Glu Asp Trp Leu Ile
            180                 185                 190

His Gln Arg Arg Pro Gln Ser Cys Lys Val Leu Val Leu Asp Ala Asp
        195                 200                 205

Leu Asn Leu Glu Asn Ile Gly Thr Glu Tyr Gln Arg Ser Glu Ser Ser
210                 215                 220

Ile Phe Asp Ala Ile Ser Ser Asn Gln Gln Pro Ser Pro Val Leu Val
225                 230                 235                 240

Ser Pro Ser Lys Arg Gln Arg Val Ala Arg
                245                 250

<210> SEQ ID NO 4
<211> LENGTH: 232
<212> TYPE: PRT
<213> ORGANISM: Homo sapiens

<400> SEQUENCE: 4

Val Gln Arg Tyr Ala Trp Pro Pro Asp Lys Glu Gln Glu Lys Glu Lys
1               5                   10                  15
```

```
Lys Ser Val Ile Cys Val Glu Gly Asn Ile Ala Ser Gly Lys Thr Thr
         20                  25                  30

Cys Leu Glu Phe Phe Ser Asn Ala Thr Asp Val Glu Val Leu Thr Glu
             35                  40                  45

Pro Val Ser Lys Trp Arg Asn Val Arg Gly His Asn Pro Leu Gly Leu
 50                  55                  60

Met Tyr His Asp Ala Ser Arg Trp Gly Leu Thr Leu Gln Thr Tyr Val
 65                  70                  75                  80

Gln Leu Thr Met Leu Asp Arg His Thr Arg Pro Gln Val Ser Ser Val
                 85                  90                  95

Arg Leu Met Glu Arg Ser Ile His Ser Ala Arg Tyr Ile Phe Val Glu
             100                 105                 110

Asn Leu Tyr Arg Ser Gly Lys Met Pro Glu Val Asp Tyr Val Val Leu
         115                 120                 125

Ser Glu Trp Phe Asp Trp Ile Leu Arg Asn Met Asp Val Ser Val Asp
130                 135                 140

Leu Ile Val Tyr Leu Arg Thr Asn Pro Glu Thr Cys Tyr Gln Arg Leu
145                 150                 155                 160

Lys Lys Arg Cys Arg Glu Glu Lys Val Ile Pro Leu Glu Tyr Leu
                165                 170                 175

Glu Ala Ile His His Leu His Glu Glu Trp Leu Ile Lys Gly Ser Leu
             180                 185                 190

Phe Pro Met Ala Ala Pro Val Leu Val Ile Glu Ala Asp His His Met
         195                 200                 205

Glu Arg Met Leu Glu Leu Phe Glu Gln Asn Arg Asp Arg Ile Leu Thr
     210                 215                 220

Pro Glu Asn Arg Lys His Cys Pro
225                 230

<210> SEQ ID NO 5
<211> LENGTH: 260
<212> TYPE: PRT
<213> ORGANISM: Artificial
<220> FEATURE:
<223> OTHER INFORMATION: Modified deoxycytidine kinase

<400> SEQUENCE: 5

Met Ala Thr Pro Pro Lys Arg Ser Cys Pro Ser Phe Ser Ala Ser Ser
 1               5                  10                  15

Glu Gly Thr Arg Ile Lys Lys Ile Ser Ile Glu Gly Asn Ile Ala Ala
             20                  25                  30

Gly Lys Ser Thr Phe Val Asn Ile Leu Lys Gln Leu Cys Glu Asp Trp
         35                  40                  45

Glu Val Val Pro Glu Pro Val Ala Arg Trp Cys Asn Val Gln Ser Thr
 50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                 85                  90                  95

Gln Thr Tyr Val Cys Leu Ser Met Ile Arg Ala Gln Leu Ala Ser Leu
             100                 105                 110

Asn Gly Lys Leu Lys Asp Ala Glu Lys Pro Val Leu Phe Phe Glu Arg
         115                 120                 125

Ser Val Tyr Ser Ala Arg Tyr Ile Phe Ala Ser Asn Leu Tyr Glu Ser
130                 135                 140
```

```
Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240

Asp Phe Lys Asp Lys Tyr Glu Ser Leu Val Glu Lys Val Lys Glu Phe
                245                 250                 255

Leu Ser Thr Leu
            260

<210> SEQ ID NO 6
<211> LENGTH: 260
<212> TYPE: PRT
<213> ORGANISM: Artificial
<220> FEATURE:
<223> OTHER INFORMATION: Modified deoxycytidine kinase

<400> SEQUENCE: 6

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
        50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Met Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Ala Arg Tyr Ile Phe Ala Ser Asn Leu Tyr Glu Ser
130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr Asn
    210                 215                 220

Phe Asp Tyr Leu Gln Glu Val Pro Ile Leu Thr Leu Asp Val Asn Glu
225                 230                 235                 240
```

```
-continued

Asp Phe Lys Asp Lys Tyr Glu Ser Leu Val Glu Lys Val Lys Glu Phe
                245                 250                 255

Leu Ser Thr Leu
            260
```

US 7,858,745 B2

USE OF SPECIFICALLY ENGINEERED ENZYMES TO ENHANCE THE EFFICACY OF PRODRUGS

This application is a continuation of U.S. patent application Ser. No. 10/791,155, filed Mar. 1, 2004 and claims the priority benefit of U.S. Provisional Application Ser. No. 60/451,207 filed Feb. 28, 2003, U.S. Provisional Application Ser. No. 60/471,660 filed May 19, 2003, U.S. Provisional Application Ser. No. 60/541,496 filed Feb. 3, 2004, and U.S. patent application Ser. No. 10/791,155, filed Mar. 1, 2004, the disclosures of all the above-mentioned applications are incorporated by reference herein.

This invention was made with U.S. Government support under National Institute of Health (NIH) grant CA095687. The U.S. Government has certain rights in the invention.

FIELD OF THE INVENTION

The invention relates to methods for enhancing efficiency of prodrugs. Specifically, the invention relates to targeted delivery of enzymes, in particular specifically engineered enzymes, to cells in need thereof. The invention is particularly directed to targeted delivery of said enzymes to cancer cells of specific tumor types. The invention specifically provides genetically-engineered mutant deoxycytidine kinase (dCK) mutants with enhanced activity towards nucleoside analogs used in cancer chemotherapy, wherein the enhanced activity is enhanced phosphorylation of nucleoside analogues. The invention also relates to modified dCK mutants with such enhanced activity, and antibody-conjugates of said enzymes that can be specifically delivered to leukemic blast cells in vivo or ex vivo.

BACKGROUND OF THE INVENTION

Many of the currently used chemotherapy agents are members of a class of drugs referred to as anti-metabolites. One type of such anti-metabolites are molecules that block or subvert one or more of the metabolic pathways involved in DNA synthesis by mimicking naturally occurring nucleic acid building blocks. Many of this type of anti-metabolites are nucleoside analogs (NAs) (wherein a nucleoside is the unphosphorylated form of a nucleotide). These NAs usually do not possess any therapeutic activity (and thus are properly termed prodrugs) and rely on their conversion, for the most part to the triphosphorylated form, to become active (prodrug to drug metabolism).

The efficiency of conversion from the administered nucleoside to the active triphosphorylated form determines the efficacy of these types of prodrugs. The serial phosphorylation of NAs to their triphosphorylated metabolite, via monophosphate and diphosphate intermediates, is catalyzed by human cellular kinases, with deoxycytidine kinase (dCK) playing a major role. dCK transfers a phosphoryl group from ATP (or other triphosphorylated nucleotides) to deoxycytidine (dC). dCK is required for the phosphorylation of numerous nucleoside analogs including AraC (1-β-D-arabinofuranosylcytosine; Cytarabine), dFdC (2',2'-difurodeoxycytidine; Gemcitabine), FaraA (2-fluoro-9-β-D-arabinosyladenine; Fludarabine) and 2CdA (2-chlorodeoxyadenosine, Cladribine) (Van Rompay, et al., 2000, *Pharmacol Ther.* 87:189-98). Therefore, the activity of dCK is one of the factors that determine the sensitivity of leukemias and solid tumors to deoxynucleoside toxicity and hence, therapy (Stegmann et al, 1995, *Blood* 85:1188-94; Lotfi et al., 1999, *Clin. Cancer Res.* 5:2438-44; Kakihara et al., 1998, *Leuk. Lymphoma* 31:405-9; Bergman et al., 1999, *Biochem. Pharmacol.* 57:397-406; Goan et al, 1999, *Cancer Res.* 59:4204-7).

The critical function of dCK for the efficacy of prodrug chemotherapy is evident from direct correlation between the enzyme's activity and drug sensitivity in tumor cell lines (Hapke et al., 1996, *Cancer Res.* 56:2343-7). Cells lacking dCK activity are resistant to a variety of drugs, including ara-C, cladribine, fludarabine and gemcitabine (Owens et al., 1992, *Cancer Res.* 52:2389-93; Ruiz van Haperen et al, 1994, *Cancer Res.* 54:4138-43) and drug sensitivity to ara-C can be restored by expressing functional dCK protein in cells that do not express this enzyme or in which only mutationally-inactivated forms thereof are expressed (Stegmann et al., 1995, *Blood* 85:1188-94). Moreover, in vivo studies conducted on animal tumors using gemcitabine showed that increased dCK activity, mediated by dCK gene transfer, results in enhanced accumulation and prolonged elimination kinetics of gemcitabine triphosphate, and ultimately, to a better tumor response to the prodrug (Blackstock et al, 2001, *Clin. Cancer Res.* 7:3263-8).

More efficient prodrug-to-drug conversion, i.e. nucleoside analog (NA) to NA-triphosphate, would greatly increase the potency of such prodrugs and reduce undesired side effects common in chemotherapeutic treatments (due at least in part to higher concentrations of the drug needed to achieve a therapeutic result, with concomitant toxicity to normal cells and tissues). Higher concentrations of the active metabolites of nucleoside analog prodrugs, particularly in the cancer cells themselves, would result in a better therapeutic index for these prodrugs. In addition, some tumor cells develop resistance to chemotherapeutic agents that are administered as prodrugs and activated by enzymes expressed in target tumor cells, by reducing or eliminating expression of the gene or genes encoding the enzymatic activity. Resistance arising from such down-regulation of cellular gene expression could be overcome by targeted delivery of the enzyme directly to the tumor cell. Thus, there is a need for more efficient enzymes and for methods of targeting those enzymes specifically to cancer cells.

SUMMARY OF THE INVENTION

The invention provides reagents and methods for targeted delivery of enzymes, in particular specifically engineered enzymes capable of converting prodrugs to biologically-active or activated forms of said prodrugs, to cells in need thereof. The invention in preferred embodiments provides said reagents and methods for targeted delivery of modified Deoxycytidine kinases (dCK), most preferably human dCK, with improved catalytic efficiency compared with wild type dCK to cells, most preferably cancer cells to produce or increase therapeutic effectiveness of nucleoside prodrugs in said cells. In a particular aspect, a modified human dCK of the invention has an amino acid sequence as set forth in SEQ ID NO: 5, which is SEQ ID NO. 1 comprising a valine residue at amino acid position 100, a methionine residue at amino acid position 104, and an alanine residue at amino acid position 133, wherein the amino acid positions are numbered according to the wild type dCK sequence (as shown in FIG. 2C, SEQ ID NO: 1).

The invention also provides said enzymes conjugated to an antibody, most preferably a monoclonal antibody or an immunologically-specific fragment thereof that is immunologically specific for and thus capable of recognizing cell surface antigens on cells, preferably tumor cells. In preferred embodiments, said enzyme-antibody conjugates specifically recognize cell surface antigens on tumor cells susceptible to the therapeutic effects of said prodrugs, wherein the therapeutic efficacy of said prodrugs are improved thereby. In alternative embodiments, said enzyme-antibody conjugates specifically recognize cell surface antigens on tumor cells not susceptible to the therapeutic effects of said prodrugs, due at least in part to lack of sufficient expression or non-expression of said enzymes endogenously in the tumor cell, wherein the therapeutic efficacy of said prodrugs is produced thereby. In most preferred embodiments, the antibody is capable of being internalized into the interior of the cell expressing the cell surface marker for which the antibody is immunologically specific. In preferred embodiments of each of these embodiments of the invention, the enzyme can activate at least one chemotherapeutic agent. In specific embodiments, the enzyme is dCK or a modified dCK as provided herein and the chemotherapeutic agent is a nucleoside analog that is a substrate of said enzyme. In one specific embodiments, the antibody is a HuM195 (Protein Design Laboratories, Fremont, Calif.) that is immunologically-specific for the cell surface antigen CD33.

The invention further provides pharmaceutical compositions comprising enzyme-antibody conjugates of the invention, most preferably at a therapeutically-effective concentration, and comprising a pharmaceutical diluent, adjuvant or excipient. In preferred embodiments, the enzyme-antibody conjugates of the invention comprise dCK, more preferably a modified dCK and most preferably a mutationally-activated, genetically engineered species of dCK as disclosed hereon, conjugated to an antibody, most preferably a monoclonal antibody that specifically recognizes a cell surface antigen expressed on the surface of a cell, most preferably a tumor cell. In additional aspects, pharmaceutical compositions according to the invention further comprise a chemotherapeutic agent, preferably a nucleoside analog most preferably one activated by the enzyme.

In addition, the invention provides methods of treating an animal, more preferably a human and most preferably a human cancer patient bearing a primary, metastatic or recurrent tumor, or a tumor exhibiting a degree of resistance to a chemotherapeutic drug. In certain embodiments of this aspect of the invention, the methods comprise the steps of: (a) administering to the patient a pharmaceutical composition of the invention comprising an antibody-conjugated enzyme capable of activating a prodrug to a chemotherapeutic drug effective against cancer cells comprising said tumor; and (b) administering a chemotherapeutic agent to the patient. In preferred embodiments, the pharmaceutical composition comprises an antibody-enzyme conjugate wherein the enzyme is dCK or, a modified species of dCK according to the invention. In preferred embodiments, the pharmaceutical composition comprises an antibody, most preferably a monoclonal antibody immunologically specific for a cell surface antigen expressed on the surface of a tumor cell. In preferred embodiments, the chemotherapeutic agent is a prodrug that is activated to an effective chemotherapeutic agent by said enzyme comprising the enzyme-antibody conjugate. In preferred embodiments, the chemotherapeutic agent is nucleoside analog. In a particular aspect, the patient has leukemia.

The invention further provides methods of using antibody-enzyme conjugates, preferably comprising dCK or a modified species of dCK according to the invention, and more preferably a pharmaceutical composition according to the invention comprising said enzyme-antibody conjugate, to treat an animal, more preferably a human and most preferably a human cancer patient. In preferred embodiments, the methods according to this aspect of the invention increase the therapeutic efficacy of a chemotherapeutic agent in a cancer patient. In certain embodiments of this aspect of the invention, the methods comprise the steps of: (a) administering to the patient a pharmaceutical composition of the invention comprising an antibody-conjugated enzyme capable of activating a prodrug to a chemotherapeutic drug effective against cancer cells comprising said tumor; and (b) administering a chemotherapeutic agent to the patient. In preferred embodiments, the pharmaceutical composition comprises an antibody-enzyme conjugate wherein the enzyme is dCK or, a modified species of dCK according to the invention. In preferred embodiments, the pharmaceutical composition comprises an antibody, most preferably a monoclonal antibody immunologically specific for a cell surface antigen expressed on the surface of a tumor cell. In most preferred embodiments, the antibody is capable of being internalized into the interior of the cell expressing the cell surface marker for which the antibody is immunologically specific. In preferred embodiments, the chemotherapeutic agent is a prodrug that is activated to an effective chemotherapeutic agent by said enzyme comprising the enzyme-antibody conjugate. In preferred embodiments, the chemotherapeutic agent is nucleoside analog. In a particular aspect, the patient has leukemia.

The invention additionally provides methods of using antibody-enzyme conjugates, preferably comprising dCK or a modified species of dCK according to the invention, and more preferably a pharmaceutical composition according to the invention comprising said enzyme-antibody conjugate, to treat an animal, more preferably a human and most preferably a human cancer patient bearing tumor cells that are resistant to a chemotherapeutic agent administered as a prodrug and activated by enzymes expressed in target tumor cells, wherein said resistant tumor cells have reduced or eliminated expression of the gene or genes encoding the enzymatic activity. In preferred embodiments, the methods according to this aspect of the invention reduce drug-resistance in tumor cells borne by the cancer patient. In certain embodiments of this aspect of the invention, the methods comprise the steps of: (a) administering to the patient a pharmaceutical composition of the invention comprising an antibody-conjugated enzyme capable of activating a prodrug to a chemotherapeutic drug effective against cancer cells comprising said tumor; and (b) administering a chemotherapeutic agent to the patient. In preferred embodiments, the pharmaceutical composition comprises an antibody-enzyme conjugate wherein the enzyme is dCK or, a modified species of dCK according to the invention. In preferred embodiments, the pharmaceutical composition comprises an antibody, most preferably a monoclonal antibody immunologically specific for a cell surface antigen expressed on the surface of a tumor cell. In most preferred embodiments, the antibody is capable of being internalized into the interior of the cell expressing the cell surface marker for which the antibody is immunologically specific. In preferred embodiments, the chemotherapeutic agent is a prodrug that is activated to an effective chemotherapeutic agent by said enzyme comprising the enzyme-antibody conjugate. In preferred embodiments, the chemotherapeutic agent is nucleoside analog. In a particular aspect, the patient has leukemia.

Specific preferred embodiments of the present invention will become evident from the following more detailed description of certain preferred embodiments and the claims.

DETAILED DESCRIPTION OF THE INVENTION

This invention provides reagents that are antibodies immunologically specific for cell surface antigens, most preferably monoclonal antibodies or immunologically-specific fragments thereof, conjugated to an enzyme, preferably a human enzyme and more preferably a human enzyme comprising a genetically-engineered or naturally-occurring mutant species thereof having an increased enzymatic activity for converting a prodrug, most preferably an anticancer prodrug into a drug species having a biological, most preferably an anticancer cell effect. In most preferred embodiments, the antibody is capable of being internalized into the interior of the cell expressing the cell surface marker for which the antibody is immunologically specific. The invention also provides methods for reducing, inhibiting or preventing proliferation of a cell, preferably a human cell and more preferably a human tumor cell, wherein the cell is contacted with the said reagents of the invention in the presence of an effective amount of a prodrug that is converted by the enzyme conjugated to the antibody comprising the reagent of the invention into a drug species having said biological, more preferably anticancer, effect. The invention also provides pharmaceutical compositions comprising said reagents, and methods of treating an animal in need thereof, more preferably a human and most preferably a human with cancer, therein a combination of one or a plurality of reagent species of the invention that are administered to the animal in the presence of a therapeutically effective amount of a prodrug that that is converted into a drug species having said biological, more preferably anticancer, effect by the enzyme conjugated to the antibody comprising the reagent of the invention.

Figure 1:
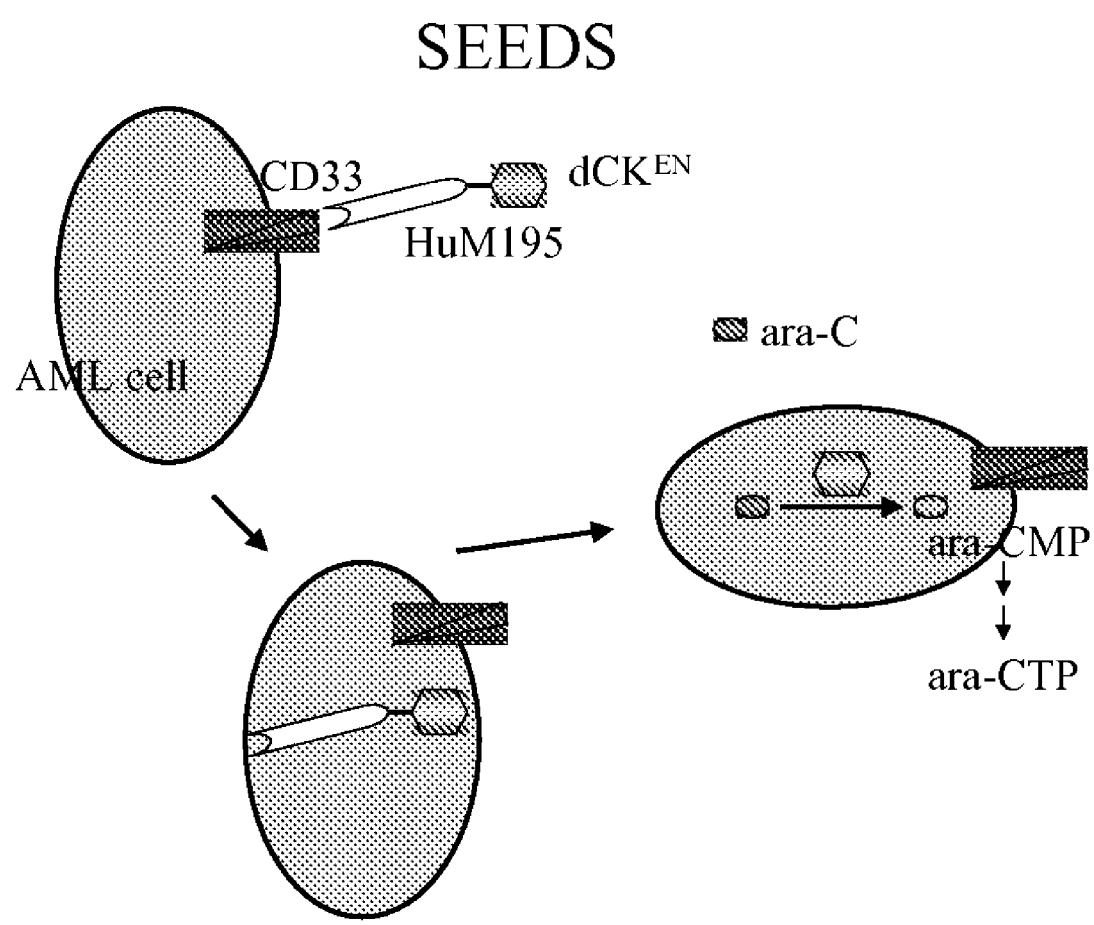
FIG. 1 is a schematic representation of certain aspects of the reagents and methods disclosed herein, termed "selective enhanced enzyme delivery system (SEEDS)".

In one embodiment, the invention provides reagents and methods of using such reagents for targeted delivery of an enzyme that can convert a prodrug to a biologically-active species thereof in a target cell. FIG. 1 shows a schematic diagram of the strategy provided by the invention. In FIG. 1, $dCK^{EN}$ is an engineered form of a nucleoside kinase, deoxycytidine kinase. $dCK^{EN}$ was designed, as described herein, to phosphorylate nucleoside analog drugs, such as AraC and gemcitabine, more efficiently, e.g., at lower extracellular concentrations, or with a greater enzymatic activity. As provided herein, the enzyme is conjugated, most preferably covalently linked, to an antibody, preferably a monoclonal antibody or immunologically-specific fragment thereof, and most preferably a human or humanized antibody immunologically specific for a cell surface antigen expressed on the cell surface of a eukaryotic cell, preferably a human cell and most preferably a human tumor cell. In most preferred embodiments, the antibody is capable of being internalized into the interior of the cell expressing the cell surface marker for which the antibody is immunologically specific.

In preferred embodiments, the antibody is a humanized antibody termed HuM195 (Protein Design Laboratories, Fremont, Calif.) that is immunologically specific for cell surface marker protein CD33. In preferred embodiments, the cell is a human leukemia cell. CD33 is primarily expressed in acute myelogenous leukemia (AML) cells, and not in normal or stem cells, thus providing targeting specificity to human tumor cells. Importantly, this antibody has the ability to internalize into the cell. In the practice of the methods of this invention, a nucleoside analog prodrug such as AraC is administered to a patient concomitantly with antibody-enzyme conjugate administration. Delivery of the enzyme to the interior of the targeted cell provides increased enzymatic activity directly thereto, and accelerates conversion of the prodrug to its monophosphate form. It is understood in the art that this monophosphorylation of the prodrug is the rate-limiting step, and that subsequent conversion of the monophosphate form to the triphosphate nucleotide is efficient in comparison. Thus, the practice of the methods of the invention with these antibody-enzyme conjugates reduces or eliminates a metabolic bottleneck experienced in the prodrug's activation, and the increased high concentration of nucleoside analogue NA-triphosphate in the targeted cell results in increased cytotoxicity in the cell.

In one embodiment, a modified dCK of the invention can be used to increase the efficacy of nucleoside analogs (NAs), such as AraC or cladribine. AraC is among the most active agents in treating acute myeloid leukemia (AML) (Estey, 2000, *Blood* 96:1670-3). The cytotoxic activity of AraC is dependent on its intracellular conversion to its active metabolite AraCTP. Sampling of blood during and after AraC therapy in patients with AML has illustrated that AraCTP levels are highly relevant to prognosis and response to therapy (Estey et al., 1987, *Leukemia* 1:580-3; Iacoboni et al, 1986, *J. Clin. Oncol.* 4:1079-88). Statistically significant correlations have been reported between response to AraC, and the rate of AraCTP elimination and the area under the curve (AUC) of AraCTP accumulation (Plunkett et al., 1985, *Semin Oncol* 12:20-30; Kantarjian et al, 1986, *Am. J. Med.* 81:387-94). This demonstrates the importance of AraCTP accumulation and retention in treatment outcome. Thus, augmentation of AraCTP levels in leukemia blasts is desirable (Gandhi et al, 1993, *J. Clin. Oncol* 11:116-24).

In certain embodiments, an antibody-conjugated enzyme of the invention can be used to target a specific tumor cell that is deficient or that lacks an active enzyme necessary for efficient drug activity. For example, dCK or a modified dCK mutant of the invention can be conjugated to an antibody (such as Herceptin) that specifically recognizes antigens on a breast tumor cell, which normally does not express dCK. The breast tumor cell can then be contacted with a nucleoside analog, thereby providing an anti-tumor effect on said cell. In particular embodiments, antibody-conjugated enzymes of the invention can be designed to target a particular tumor cell type by choosing an antibody that specifically recognizes antigens on that tumor cell. For example, for prostate cancer, antibodies can be chosen that recognize STEAP (six-transmembrane epithelial antigen of the prostate; Hubert et al., 1999, *Proc Natl Acad Sci USA*. 7:4523-8).

Thus, in one embodiment, the invention provides methods for sensitizing tumor cells that are non-responsive to particular drugs by generating an antibody-conjugated enzyme that will deliver the enzyme to the tumor cells thereby expressing the enzyme that can activate the particular drug in the cells. A non-responsive cell can be, for example, a cell that normally does not express or expresses an insufficient amount of the necessary enzyme, a cell that expresses a defective enzyme, and/or a cell that has acquired resistance to a particular drug (i.e. continues to grow in the presence of a drug that previously diminished or inhibited growth of the cell).

In certain embodiments, an antibody of the invention can be an antibody that is known to recognize antigens specific to a certain cell type including, but not limited to, antibodies described in Sandlie and Brekke (2003, *Nat. Rev. Drug Discovery* 2:52-62). Alternatively, antibodies useful in the invention can be generated to recognize a desired antigen using techniques described herein. In certain aspects of these embodiments, the antibody can internalize or be internalized within the target cell (i.e. enter the target cell through the cell membrane) so that an enzyme conjugated to the antibody is active in the cytoplasm of the target cell. In other aspects, the antibody can bind to a target cell but not internalize, so that a conjugated enzyme is not internalized within the target cell but can activate prodrugs that will enter the target cell in an activated state. In still other aspects, the antibody can be engineered to comprise a Protein Transduction Domain (PTD), which is a short stretch of amino acids, mainly basic amino acids such as arginine, that can carry a protein inside a cell (see, for example, Kabouridis, 2003, *Trends in Biotechnology* 21:498-503).

Disclosed herein is a particular embodiment of a modified human dCK species having increased kinase activity. Those with skill in the art will appreciate that other modified species having increased kinase activity can be produced using the methods disclosed herein, and fall within the scope of the instant disclosure. Included within said modified species are preferably species genetically engineered to have increased activity, but naturally-occurring variants of human dCK are explicitly considered to fall within the scope of the instant disclosure.

All references cited in this application are expressly incorporated by reference herein for any purpose. In the preparation of the reagents of this invention, in the preparation of the pharmaceutical formulations of the invention, and in the practice of the methods of the invention utilizing said reagents and pharmaceutical formulations certain techniques and experimental methods in the chemical, biological, pharmaceutical and recombinant genetics arts are used in accordance with the understanding of those having skill in the art and as set forth herein.

Conventional techniques may be used for recombinant DNA preparation, oligonucleotide synthesis, and in vitro cell and tissue culture and transformation (e.g., electroporation, lipofection). Enzymatic reactions and purification techniques may be performed according to manufacturer's specifications or as commonly accomplished in the art or as described herein. The aforesaid techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "isolated polynucleotide" as used herein shall mean a polynucleotide of genomic DNA, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of synthetic origin, or any combination thereof. Preferably, the isolated protein is substantially free from proteins or polypeptides or other contaminants that are found in its natural environment that would interfere with its use (therapeutic, diagnostic, prophylactic, research or otherwise).

The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. Thus, a "polypeptide" or a "protein" can comprise one (termed "a monomer") or a plurality (termed "a multimer") of amino acid chains. The terms "polypeptide" and "protein" specifically encompass deoxycytidine kinase (dCK) and modified forms thereof, and particularly genetically-engineered species of dCK produced as disclosed herein, or sequences that have deletions from, additions to, and/or substitutions of one or more amino acid of dCK or a modified dCK of the invention.

The term "polypeptide fragment" refers to a polypeptide, which can be monomeric or multimeric, having an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 8, 10, 14, 20, 50, 70, 100, 110, 150, 200, 250, 300, 350, 400, or 450 amino acids long. Particularly useful polypeptide fragments include functional domains, including binding domains.

The term "naturally-occurring" as used herein and applied to an object refers to the fact that the object can be found in nature. For example, a polypeptide or polynucleotide sequence that is present in an organism (including viruses) that can be isolated from a source in nature and that has not been intentionally modified by man is naturally-occurring.

The term "operably linked" means that the components to which the term is applied are in a relationship that allows them to carry out their inherent functions under suitable conditions. For example, a transcription control sequence "operably linked" to a protein coding sequence is covalently ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as used herein means single-stranded or double-stranded nucleic acid polymers of at least 10 bases in length. In certain embodiments, the nucleotides comprising the polynucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "oligonucleotide" referred to herein includes naturally occurring, and modified nucleotides linked together by naturally occurring, and/or non-naturally occurring oligonucleotide linkages. Oligonucleotides are a polynucleotide subset comprising members that are generally single-stranded and have a length of 200 bases or fewer. In certain embodiments, oligonucleotides are 10 to 60 bases in length. In certain embodiments, oligonucleotides are 12, 13, 14, 15, 16, 17, 18, 19, or 20 to 40 bases in length. Oligonucleotides may be single stranded or double stranded, e.g. for use in the construction of a gene mutant. Oligonucleotides of the invention may be sense or antisense oligonucleotides with reference to a protein-coding sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

The term "recombinant expression construct" as used herein is a replicable DNA construct in which a DNA sequence encoding a protein or polypeptide according to the invention is operably linked to suitable control sequences capable of effecting the expression of the protein or polypeptide in a suitable host cell. The need for such control sequences will vary depending upon the host selected and the transformation method chosen. Generally, control sequences include a transcriptional promoter, an optional operator or enhancer sequence to control or regulate transcription, a sequence encoding suitable mRNA ribosomal binding sites, and sequences which control the termination of transcription and translation, and in mammalian cells, sequences that direct 5' terminal capping and 3' terminal polyadenylation of the primary transcript. Amplification vectors, on the other hand, do not require expression control domains. All that is needed is the ability to replicate in a host, usually conferred by an origin of replication, and a selection gene to facilitate recognition of transformants. See, Sambrook et al., 2001, *Molecular Cloning: A Laboratory Manual* (Cold Spring Harbor Press: New York).

The term "host cell" is used to refer to a cell into which has been introduced, or is capable of being introduced with a nucleic acid sequence and further expresses or is capable of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

The term "identity," as known in the art, refers to a relationship between the sequences of two or more polypeptide molecules or two or more nucleic acid molecules, as determined by comparing the sequences thereof. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is used in the art with regard to a related concept, but in contrast to "identity," "similarity" refers to a measure of relatedness, which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al., 1988, *SIAM J. Applied Math.*, 48:1073; and Durbin et al., 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al., 1984, *Nucl. Acid. Res.*, 12:387; Genetics Computer Group, University of Wisconsin, Madison, Wis.), BLASTP, BLASTN, and FASTA (Altschul et al., 1990, *J. Mol. Biol.*, 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990, supra). The well-known Smith Waterman algorithm may also be used to determine identity.

Certain alignment schemes for aligning two amino acid or polynucleotide sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide. In some embodiments, the alignment can comprise at least 60, 70, 80, 90, 100, 110, or 120 amino acids of the target polypeptide. If polynucleotides are aligned using GAP, the alignment can span at least about 100, 150, or 200 nucleotides, which can be contiguous.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as three-times the average diagonal; where the "average diagonal" is the average of the diagonal of the comparison matrix being used; the "diagonal" is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al., 1978, *Atlas of Protein Sequence and Structure*, 5:345-352 for the PAM 250 comparison matrix; Henikoff et al., 1992, *Proc. Natl. Acad. Sci USA*, 89:10915-10919 for the BLOSUM 62 comparison matrix) is also used by the algorithm.

In certain embodiments, the parameters for a polypeptide sequence comparison include the following:

Algorithm: Needleman et al., 1970, *J. Mol. Biol.*, 48:443-453;

Comparison matrix: BLOSUM 62 from Henikoff et al., 1992, supra;

Gap Penalty: 12

Gap Length Penalty: 4

Threshold of Similarity: 0

The GAP program may be useful with the above parameters. For nucleotide sequences, parameters can include a gap penalty of 50 and a gap length penalty of 3, that is a penalty of 3 for each symbol in each gap. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

1) hydrophobic: norleucine (Nor), Met, Ala, Val, Leu, Ile;
2) neutral hydrophilic: Cys, Ser, Thr, Asn, Gln;
3) acidic: Asp, Glu;
4) basic: H is, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See, for example, Moult, 1996, *Curr. Op. in Biotech.* 7:422-427; Chou et al., 1974, *Biochemistry* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See Holm, 1999, supra; and Brenner, 1997, supra).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W. H. Freeman and Company, New York; INTRODUCTION TO PROTEIN STRUCTURE (C. Branden and J. Tooze, eds.), 1991, Garland Publishing, New York, N.Y.; and Thornton et al., 1991, *Nature* 354:105, each of which are incorporated herein by reference.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid, or attachment to a polypeptide or nucleic acid of a fluorescent marker, a chemiluminescent marker or an enzyme having a detectable activity, or attachment to a polypeptide of biotin moieties that can be detected by labeled avidin (e.g., streptavidin preferably comprising a detectable marker such as a fluorescent marker, a chemiluminescent marker or an enzymatic activity that can be detected, inter alia, by optical or colorimetric methods). In certain embodiments, the label can also be therapeutic. Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}H$, $^{14}C$, $^{15}N$, $^{35}S$, $^{90}Y$, $^{99m}Tc$, $^{111}In$, $^{125}I$, $^{131}I$), fluorescent labels (e.g., fluorescein isothiocyanate or FITC, rhodamine, or lanthamide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, or epitope tags). In certain embodiments, labels are attached by spacer arms (such as $(CH_2)_n$, where n<about 20) of various lengths to reduce potential steric hindrance.

The term "biological sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent or drug" as used herein refers to a chemical compound or composition capable of inducing a desired therapeutic effect when properly administered to a patient.

The term "chemotherapeutic agent" as used herein refers to a drug or pharmaceutical agent that is used to treat a cancer patient, including but not limited to, nucleoside analogs. A "nucleoside analog" can be, for example, AraC (1-β-D-arabinofuranosylcytosine; Cytarabine), dFdC (2',2'-difurodeoxycytidine; Gemcitabine), FaraA (2-fluoro-9-β-D-arabinosyladenine; Fludarabine), ddC (2',3'-dideoxycytidine; Zalcitabine), 3TC (2'-deoxy-3'-thiacytidine; Lamivudine), and 2CdA (2-chlorodeoxyadenosine, Cladribine).

Treatment of a cancer patient, as described herein, encompasses alleviation of at least one symptom of the cancer, a reduction in the severity of the cancer, or the delay or prevention of progression of the cancer. Treatment need not mean that the cancer is totally cured. A useful therapeutic agent of the invention needs only to reduce the severity of a cancer, reduce the severity of a symptom or symptoms associated with the cancer or its treatment, or provide improvement to a patient's quality of life, or delay or prevent progression of the cancer.

The invention encompasses a method of treating an animal, preferably a human with cancer comprising administering to the cancer patient an antibody-conjugated enzyme of the invention, more preferably a pharmaceutical composition of the invention comprising an antibody-conjugated enzyme of the invention, and most preferably wherein the an antibody-conjugated enzyme of the invention comprises a modified deoxycytidine kinase (dCK) of the invention, in an amount and for a time sufficient to induce a sustained improvement when compared to the patient or tumor before treatment of an indicator that reflects the severity of a particular cancer or the severity of symptoms caused by the cancer or that delays or prevents progression of the cancer. The invention does not exclude possible treatment with other therapeutic agents before, after, and/or during treatment with the antibody-conjugated enzyme of the invention, a pharmaceutical composition of the invention, or a modified deoxycytidine kinase (dCK) of the invention.

As used herein, the terms "substantially pure" or "substantially purified" mean a compound or species that is the predominant species present (i.e., on a molar basis it is more abundant than any other individual species in the composition). In certain embodiments, a substantially purified fraction is a composition wherein the species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the species is purified to essential homogeneity (contaminant species cannot be detected in the composition by conventional detection methods) wherein the composition consists essentially of a single macromolecular species.

The term "patient" as used herein includes human and animal subjects, but human patients are preferred, and most preferred are human cancer patients.

Unless otherwise required by context, singular terms shall include pluralities.

As used herein, the terms "antibody" or "antibody peptide(s)" refer to a monomeric or multimeric protein comprising one or more polypeptide chains. An antibody can bind specifically to an antigen and may be able to inhibit or modulate the biological activity of the antigen. "Antibodies" include naturally occurring antibodies, which are described below. In certain embodiments, antibodies are produced by recombinant DNA techniques. In additional embodiments, the term "antibodies" encompasses fragments of naturally-occurring or synthetic antibodies that are produced by enzymatic or chemical cleavage of naturally occurring antibodies. Antibody fragments include, but are not limited to, F(ab), F(ab'), F(ab')$_2$, Fv, and single chain Fv fragments. Antibodies and antibody fragments as these terms are used herein also include single-chain, chimeric, humanized, fully human, polyclonal, and monoclonal antibodies. At a minimum, an antibody, as meant herein, comprises a polypeptide that can bind specifically to an antigen wherein the antibody comprises all or part of a light or heavy chain variable region.

A variable region comprises at least three heavy or light chain complementarity determining regions (CDRs, also known as hypervariable regions, designated CDR1, CDR2, and CDR3 by Kabat et al., 1991, Sequences of Proteins of Immunological Interest, Public Health Service N.I.H., Bethesda, Md.; see also Chothia and Lesk, 1987, J. Mol. Biol. 196: 901-17; Chothia et al., 1989, Nature 342: 877-83) embedded within a framework region (designated framework regions 1-4, FR1, FR2, FR3, and FR4, by Kabat et al., supra; see also Chothia and Lesk, supra). The CDRs and the framework segments are interspersed as follows, starting at the amino terminus of the variable region: FR1-CDR1-FR2-CDR2-FR3-CDR3-FR4.

The term "heavy chain" includes any immunoglobulin polypeptide having sufficient variable region sequence to confer binding specificity for a particular antigen. The term "light chain" includes any immunoglobulin polypeptide having sufficient variable region sequence to confer binding specificity for a particular antigen. Such a heavy or light chain may, but need not, bind to an antigen in the absence of a light chain, if it is a heavy chain, or a heavy chain, if it is a light chain. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxyl-terminus. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof. An F(ab) fragment is comprised of one light chain and the $C_H1$ and variable regions of one heavy chain. The heavy chain of an F(ab) molecule cannot form a disulfide bond with another heavy chain molecule. An F(ab') fragment contains one light chain and one heavy chain that contains more of the constant region, between the $C_H1$ and $C_H2$ domains, such that an interchain disulfide bond can be formed between two heavy chains to form an F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203.

The invention also encompasses fully human, humanized, and chimeric antibodies. As used herein, the term "fully human antibodies" comprise amino acid sequences encoded only by polynucleotides that are ultimately of human origin or amino acid sequences that are identical to such sequences. For example, inter alia, antibodies encoded by human immunoglobulin-encoding DNA inserted into a mouse genome produced in a transgenic mouse are fully human antibodies since they are encoded by DNA that is ultimately of human origin. In this situation, human immunoglobulin-encoding DNA can be rearranged (to encode an antibody) within the mouse, and somatic mutations may also occur. Antibodies encoded by originally human DNA that has undergone such changes in a mouse are fully human antibodies as the term is used herein. The use of such transgenic mice makes it possible to select fully human antibodies against a human antigen. One of skill in the art will appreciate that fully human antibodies are advantageous for use as therapeutics, particularly to treat chronic diseases, since they are unlikely to precipitate an immune response against themselves. In contrast, many non-human antibodies are known to precipitate an immune response against themselves when used in humans, a situation that makes chronic use of such antibodies in humans inadvisable. Fully human antibodies thus solve a long-standing problem faced in using antibodies to treat chronic conditions, including human diseases. See e.g. Billiau, 1988, *Immunol Today* 9:37-40; Horneff et al., 1991, *Clin. Immunol. & Immunopathol.* 59:89-103; Tjandra et al., 1990, *Immunol & Cell Biol.* 68:367-76.

In a humanized antibody, the entire antibody, except the CDRs, is encoded by a polynucleotide of human origin or is identical to such an antibody except within its CDRs. The CDRs, which are encoded by nucleic acids originating in a non-human organism, are grafted into the β-sheet framework of a human antibody variable region to create an antibody, the specificity of which is determined by the engrafted CDRs. The creation of such antibodies is described in, e.g., WO 92/11018, Jones et al., 1986, *Nature* 321:522-25, Verhoeyen et al., 1988, *Science* 239:1534-36. In contrast, a chimeric antibody comprises a human constant region (which is encoded by a polynucleotide of human origin or is identical to such a human constant region) and a non-human variable region. The creation of such antibodies is described in, e.g., U.S. Pat. No. 5,681,722.

A bivalent antibody other than a "multispecific" or "multifunctional" antibody, in certain embodiments, is understood to comprise binding sites having identical antigenic specificity. A bispecific or bifunctional antibody typically is an artificial hybrid antibody having two different heavy chain/light chain pairs and two different binding sites. Bispecific antibodies may be produced by a variety of methods including, but not limited to, fusion of hybridomas or linking of F(ab') fragments. See, e.g., Songsivilai & Lachmann, 1990, *Clin. Exp. Immunol.* 79: 315-321; Kostelny et al., 1992, *J. Immunol.* 148:1547-1553.

In additional embodiments, antibody variants can include antibodies comprising a modified Fc fragment or a modified heavy chain constant region. An Fc fragment or a heavy chain constant region can be modified by mutation to confer on an antibody altered characteristics. See, for example, Burton and Woof, 1992, *Advances in Immunology* 51: 1-84; Ravetch and Bolland, 2001, *Annu. Rev. Immunol.* 19: 275-90; Shields et al., 2001, *Journal of Biol. Chem.* 276: 6591-6604; Telleman and Junghans, 2000, *Immunology* 100: 245-251; Medesan et al., 1998, *Eur. J. Immunol.* 28: 2092-2100; all of which are incorporated herein by reference). Such mutations can include substitutions, additions, deletions, or any combination thereof, and are typically produced by site-directed mutagenesis using one or more mutagenic oligonucleotide(s) according to methods described herein, as well as according to methods known in the art (see, for example, Maniatis et al., MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

Additional antibody variants include cysteine variants wherein one or more cysteine residues are deleted from or substituted for another amino acid (e.g., serine) compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

The ability to clone and reconstruct megabase-sized human loci in yeast artificial chromosomes (YACs) and to introduce them into the mouse germline permits development of an advantageous approach to elucidating the functional components of very large or crudely mapped loci as well as generating useful models of human disease. Furthermore, the utilization of such technology for substitution of mouse loci with their human equivalents produces unique insights into the expression and regulation of human gene products during development, their communication with other systems, and their involvement in disease induction and progression.

An important practical application of such a strategy is the alteration of the mouse humoral immune system by the introduction of human immunoglobulin (Ig) loci into mice in which the endogenous Ig genes have been inactivated. International Application No. WO 93/12227. This system offers the opportunity to study mechanisms underlying programmed expression and assembly of antibodies as well as their role in B-cell development. Furthermore, such a strategy provides a source for production of fully human monoclonal antibodies (MAbs). Fully human MAbs are expected to minimize the immunogenic and allergic responses intrinsic to mouse or mouse-derived MAbs, and to thereby increase the efficacy and safety of the administered antibodies.

Using methods set forth herein, one skilled in the art can engineer mouse strains deficient in mouse antibody production with large fragments of the human Ig loci so that such mice produce human antibodies in the absence of mouse antibodies. Large human Ig fragments may preserve the large variable gene diversity as well as the proper regulation of antibody production and expression. By exploiting the mouse cellular machinery for antibody diversification and selection and the lack of immunological tolerance to human proteins, the reproduced human antibody repertoire in these mouse strains yields high affinity antibodies against any antigen of interest, including human antigens. Using the hybridoma technology, antigen-specific human MAbs with the desired specificity may be produced and selected.

In certain embodiments, the skilled artisan can use constant regions from species other than human along with the human variable region(s) in such mice to produce chimeric antibodies.

Antibodies can be matured in vitro to produce antibodies with altered properties, such as a higher affinity for an antigen or a lower dissociation constant. Variation of only residues within the complementarity determining regions (CDRs), particularly the CDR3s, can result in altered antibodies that bind to the same antigen, but with greater affinity. See e.g. Schier et al., 1996, *J. Mol. Biol.* 263:551-67; Yang et al., 1995, *J. Mol. Biol.* 254:392-403. The invention encompasses antibodies created by a variety of in vitro selection schemes, such as affinity maturation and/or chain shuffling (Kang et al., 1991, *Proc. Natl. Acad. Sci.* 88:11120-23), or DNA shuffling (Stemmer, 1994, *Nature* 370:389-391), by which antibodies may be selected to have advantageous properties. In many schemes, a known antibody is randomized at certain positions, often within the CDRs, in vitro and subjected to a selection process whereby antibodies with desired properties, such as increased affinity for a certain antigen, can be isolated. See e.g. van den Beucken et al., 2001, *J. Mol. Biol.* 310:591-601; Desiderio et al., 2001, *J. Mol. Biol.* 310:603-15; Yang et al., 1995, *J. Mol. Biol.* 254:392-403; Schier et al., 1996, *J. Mol. Biol.* 263:551-67. Typically, such mutated antibodies may comprise several altered residues in one or more CDRs, depending on the design of the mutagenesis and selection steps. See e.g. van den Beucken et al., supra.

Preferred antibodies of the invention are specific for antigens present on the cell surface of target cells, most preferably tumor cells. Most preferred embodiments of said antibodies are not immunogenic, and are capable of being internalized within the target tumor cells. The antibodies chosen for conjugation to a particular enzyme will depend on the type of cancer cell that is to be targeted. Said antibodies are preferably conjugated to an enzyme that catalyzes production of a biologically-active drug from a prodrug having reduced or little activity compare with the active drug. In certain embodiments of this invention, the antibodies are conjugated to deoxycytidine kinase (dCK), more preferably human dCK and most preferably modified human deoxycytidine kinase as disclosed herein. Antibodies used in such conjugates most preferably are effectively internalized within a targeted cell. Such antibodies are known, such as HuM195 used in acute myelogenous leukaemia (AML) therapy and BL22 used in therapy of B-cell malignancies (Caron et al, 1992, *Cancer Res.* 52:6761-7; Appelbaum, 1999, *Semin Hematol* 36:2-8). Alternatively, such antibodies can be designed to identify specific cells.

In a preferred embodiment, the invention provides covalent conjugates of a humanized anti-CD33 monoclonal antibody, can be used to target leukemia blast cells, most preferably acute myelogenous leukaemia blast cells. In additional embodiments, the invention provides antibody-conjugated enzymes that can target any tumor cell by choosing an antibody that will bind to antigens on that tumor cell. For example, in addition to anti-CD33 antibodies for leukaemia cells, anti-CD20 (such as Rituxan) antibodies can be used to target tumor cells of Non-Hodgkin's lymphoma, Herceptin antibodies can be used to target breast tumor cells, and anti-CC49 antibodies (such as B72.3) can be used to target colorectal, ovarian, and breast tumor cells. Non-limiting examples of these and additional antibodies useful for designing antibody-conjugated enzymes of the invention are described in Sandlie and Brekke (2003, *Nat. Rev. Drug Discovery* 2:52-62). In particularly preferred embodiments, antibody-conjugated enzymes according to the invention are effectively delivered into a targeted cell.

Antibodies of the invention can be polyclonal or monoclonal and/or may be recombinant antibodies. In certain embodiments, fully human antibodies of the invention are prepared, for example, by immunization of transgenic animals capable of producing human antibodies (see, for example, International Patent Application, Publication WO 93/12227).

Antibodies of the invention can be prepared using transgenic mice that have a substantial portion of the human antibody producing locus inserted in antibody-producing cells of the mice, and that are further engineered to be deficient in producing endogenous, murine, antibodies. Such mice are capable of producing human immunoglobulin molecules and antibodies and do not produce or produce substantially reduced amounts of murine immunoglobulin molecules and antibodies. Technologies utilized for achieving this result are disclosed in the patents, applications, and references disclosed in the specification herein. In certain embodiments, the skilled worker may employ methods as disclosed in International Patent Application Publication No. WO 98/24893, which is hereby incorporated by reference for any purpose. See also Mendez et al., 1997, *Nature Genetics* 15:146-156, which is hereby incorporated by reference for any purpose.

The monoclonal antibodies (mAbs) of the invention can be produced by a variety of techniques, including conventional monoclonal antibody methodology, e.g., the standard somatic cell hybridization technique of Kohler and Milstein (1975, *Nature* 256:495). Although somatic cell hybridization procedures are preferred, in principle, other techniques for producing monoclonal antibodies can be employed, e.g., viral or oncogenic transformation of B-lymphocytes. A conventional animal system useful for preparing hybridomas is the mouse. Hybridoma production in the mouse is very well established, and immunization protocols and techniques for isolation of immunized splenocytes for fusion are well known in the art. Fusion partners (e.g., murine myeloma cells) and fusion procedures are also known.

In certain embodiments, conservative modifications to the heavy chains and light chains of an antibody of the invention (and corresponding modifications to the encoding nucleotides) can produce antibodies having functional and chemical characteristics similar to those of the wild type antibody. In contrast, substantial modifications in the functional and/or chemical characteristics of an antibody may be accomplished by selecting substitutions in the amino acid sequence of the heavy and light chains that differ significantly in their effect on maintaining (a) the structure of the molecular backbone in the area of the substitution, for example, as a β sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Desired amino acid substitutions (whether conservative or non-conservative) can be determined by those skilled in the art at the time such substitutions are desired. In certain embodiments, amino acid substitutions can be used to identify important residues of an antibody, or to increase or decrease the affinity of the antibodies of the invention.

Conjugation of an antibody to an enzyme can be accomplished using techniques as described in the Examples below.

In certain embodiments of the reagents of the invention are provided modified species of rate-limiting kinases that activate nucleoside analogs (NAs) with improved kinetic properties compared with the naturally-occurring species of said kinases. In preferred embodiments, the modified versions comprise genetically-engineered species of the kinase having been modified at selected residues identified by sequence comparison with ortholog kinases from other species. The invention further provides methods for designing the modified species of such kinases. In alternative embodiments the modified versions are mutants, either naturally-occurring or the result of screening or selection protocols using mutagenesis methods well known to those with skill in the art. In other embodiments, the invention provides methods of introducing such modified enzymes into cells, preferably human cells, and more preferably human cancer cells or drug-resistant human cancer cells, thereby increasing the therapeutic potency of these molecules. In particularly preferred embodiments, such modified enzyme species are covalently linked to an antibody, preferably a monoclonal antibody or immunologically specific fragment thereof, that is immunologically specific for an antigen expressed at the cell surface of a target cell, whereby the antibody-enzyme conjugate is specifically targeted and selectively delivered to a cell, preferably a human cell and most preferably a human tumor cell or drug resistant variant thereof. Preferably, the immunological specificity of the antibody specifically targets the conjugate to the particular cancer cell for which the patient needs treatment. Advantageously, the immunological specificity provides an improved degree of discrimination of action between cancer and healthy cells.

The structures of human dCK in complex with dC-ADP, ara-C-ADP•Mg, and gemcitabine-ADP•Mg have been determined and are described herein. These structures were advantageously used to elucidate the structures of the human dCK enzyme and phosphorylation kinetics observed with various cytosine-analogs and suggested specific modifications to the current arsenal of prodrugs that may improve phosphorylation by dCK, thereby providing an improved therapeutic index. The dCK complexes described herein can be used in structure-based design of mutant enzymes with enhanced activity, which can be used, for example, in gene therapy applications.

In addition, the protein structures can be used to guide the development of improved anticancer molecules. Such molecules are termed chemical mimetic, organomimetics or peptidomimetics as understood by those having skill in the art. As used herein, the terms "mimetic," "peptide mimetic," "peptidomimetic," "organomimetic" and "chemical mimetic" are intended to encompass chemical compounds having an arrangement of atoms is a three-dimensional orientation that is equivalent to that of a nucleoside analog prodrug. It will be understood that the phrase "equivalent to" as used herein is intended to encompass compounds having substitution of certain atoms or chemical moieties in said peptide with moieties having bond lengths, bond angles and arrangements thereof in the mimetic compound that produce the same or sufficiently similar arrangement or orientation of said atoms and moieties to have the biological function of the prodrug. These terms are used according to the understanding in the art, as illustrated for example by Fauchere, 1986, *Adv. Drug Res.* 15: 29; Veber & Freidinger, 1985, *TINS* p. 392; and Evans et al., 1987, *J. Med. Chem.* 30: 1229, incorporated herein by reference.

In accordance with the methods of conventional drug design, the desired mimetic molecules are obtained by randomly testing molecules whose structures have an attribute in common with the structure of a "native" prodrug. The quantitative contribution that results from a change in a particular group of a binding molecule can be determined by measuring the biological activity of the putative mimetic in comparison with the tumor-inhibiting activity of the prodrug. In a preferred embodiment of rational drug design, the mimetic is designed to share an attribute of the most stable three-dimensional conformation of the prodrug. Thus, for example, the mimetic may be designed to possess chemical groups that are oriented in a way sufficient to cause ionic, hydrophobic, or van der Waals interactions that are similar to those exhibited by the tumor-inhibiting prodrugs of the invention, as disclosed herein.

The preferred method for performing rational mimetic design employs a computer system capable of forming a representation of the three-dimensional structure of the prodrug, such as those exemplified by Hol, 1989a, ibid.; Hol, 1989b, ibid.; and Hol, 1986, ibid. Molecular structures of the peptido-, organo- and chemical mimetics of the prodrugs of the invention are produced according to those with skill in the art using computer-assisted design programs commercially available in the art. Examples of such programs include SYBYL 6.5®, HQSAR™, and ALCHEMY 2000™ (Tripos); GALAXY™ and AM2000 (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.) and CHEMBUILDER3D™ (Interactive Simulations, Inc., San Diego, Calif.).

The peptido-, organo- and chemical mimetics produced using the prodrugs disclosed herein using, for example, art-recognized molecular modeling programs are produced using conventional chemical synthetic techniques, most preferably designed to accommodate high throughput screening, including combinatorial chemistry methods. Combinatorial methods useful in the production of the peptido-, organo- and chemical mimetics of the invention include phage display arrays, solid-phase synthesis and combinatorial chemistry arrays, as provided, for example, by SIDDCO, Tuscon, Ariz.; Tripos, Inc.; Calbiochem/Novabiochem, San Diego, Calif.; Symyx Technologies, Inc., Santa Clara, Calif.; Medichem Research, Inc., Lemont, Ill.; Pharm-Eco Laboratories, Inc., Bethlehem, Pa.; or N.V. Organon, Oss, Netherlands. Combinatorial chemistry production of the peptido-, organo- and chemical mimetics of the invention are produced according to methods known in the art, including but not limited to techniques disclosed in Terrett, 1998, COMBINATORIAL CHEMISTRY, Oxford University Press, London; Gallop et al., 1994, "Applications of combinatorial technologies to drug discovery. 1. Background and peptide combinatorial libraries," *J. Med.*

Chem. 37: 1233-51; Gordon et al., 1994, "Applications of combinatorial technologies to drug discovery. 2. Combinatorial organic synthesis, library screening strategies, and future directions," *J. Med. Chem.* 37: 1385-1401; Look et al., 1996, *Bioorg. Med. Chem. Lett.* 6: 707-12; Ruhland et al., 1996, *J. Amer. Chem. Soc.* 118: 253-4; Gordon et al., 1996, *Acc. Chem. Res.* 29: 144-54; Thompson & Ellman, 1996, *Chem. Rev.* 96: 555-600; Fruchtel & Jung, 1996, *Angew. Chem. Int. Ed. Engl.* 35: 17-42; Pavia, 1995, "The Chemical Generation of Molecular Diversity", Network Science Center, www.netsci.org; Adnan et al., 1995, "Solid Support Combinatorial Chemistry in Lead Discovery and SAR Optimization," Id., Davies and Briant, 1995, "Combinatorial Chemistry Library Design using Pharmacophore Diversity," Id., Pavia, 1996, "Chemically Generated Screening Libraries: Present and Future," Id.; and U.S. Pat. Nos. 5,880,972 to Horlbeck; 5,463,564 to Agrafiotis et al.; 5,331,573 to Balaji et al.; and 5,573,905 to Lerner et al.

In one embodiment, the invention provides a dCK mutant having greater catalytic activity than naturally-occurring wild type enzyme, in particular ~50-fold more efficient in phosphorylating dC and ~4-fold in activating gemcitabine.

The structural information provided herein can be used to design additional dCK mutants with enhanced activity towards clinically important nucleoside analogs (NAs), which can be used in modulating conventional chemotherapy. Hematopoietic progenitor cell assays as disclosed herein can be used to examine the effect of such modified dCK mutants on the cytotoxicity of NAs such as AraC.

In one embodiment, structural information of the dCK complexes described herein can be used for structure-based design of the modified dCK enzymes or other NA-prodrug-activating enzymes useful according to the invention. Various methods of structure-based drug design are disclosed in the art, for example, in Maulik et al., 1997, Molecular Biotechnology: Therapeutic Applications and Strategies, Wiley-Liss, Inc., which is incorporated herein by reference in its entirety. Maulik et al. disclose, for example, methods of directed design, in which a user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Several computer programs are known in the art that can be used in designing a potential inhibitor of the invention, including, but not limited to: GRID (Goodford, 1985, *J. Med. Chem.* 28:849-857); MCSS (Miranker and Karplus, 1991, *Proteins: Structure, Function and Genetics* 11:29-34); AUTODOCK (Goodsell and Olsen, 1990, *Proteins: Structure, Function, and Genetics* 8:195-202); DOCK (Kuntz et al., 1982, *J. Mol. Biol.* 161: 269-288); ALADDIN (Van Drie et al., 1989, *J. Comp-Aided Mol. Des.* 3:225); CLIX (Davie and Lawrence, 1992, *Proteins* 12:31-41); GROUPBUILD (Rotstein and Murcko, 1993, *J. Med. Chem.* 36:1700); GROW (Moon and Howe, 1991, *Proteins* 11:314); LUDI (Bohm, 1992, *J. Comp. Aid. Molec. Design* 6:61-78; and Rotstein and Murcko, 1992, *J. Med. Chem.* 36:1700-1710); LEGEND (Nishibata and Itai, 1991, *Tetrahedron* 47:8985); and LeapFrog (available from Tripos Associates, St. Louis, Mo.).

Other molecular modeling techniques can also be used in accordance with the invention, including, but not limited to, Cohen et al., 1990, *J. Med. Chem.* 33:883-894; Navia and Murcko, 1992, *Current Opinions in Structural Biology* 2:202-210; and Jorgensen, 1998, "BOSS-Biochemical and Organic Simulation System" in the Encyclopedia of Computational Chemistry (P. V. R. Schleyer, ed.) Wiley & Sonstra., Athens, U.S.A. 5:3281-3285).

Nucleic acid molecules (or polynucleotides) encoding the amino acid sequence of deoxycytidine kinase (dCK) or a modified dCK that has a better catalytic efficiency than wild type dCK are encompassed by the invention. Such polynucleotides can be inserted into an appropriate expression vector using conventional recombinant genetic techniques. The vector is typically selected to be functional in the particular host cell employed (i.e., the vector is compatible with the host cell machinery such that amplification of the gene and/or expression of the gene can occur). For a review of expression vectors, see METH. ENZ. 185 (Goeddel, ed.), 1990, Academic Press.

Typically, recombinant expression constructs comprising expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the construct may contain a "tag"-encoding sequence, i.e., an oligonucleotide molecule located at the 5' or 3' end of a modified dCK polypeptide coding sequence; the oligonucleotide sequence encodes polyHis (such as hexa-His), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the dCK or modified dCK of the invention from the host cell. Affinity purification can be accomplished, for example, by column chromatography using antibodies against the tag as an affinity matrix. Optionally, the tag can subsequently be removed from the purified dCK or modified dCK polypeptide by various means such as using certain peptidases for cleavage. For example, human dCK can be tagged with a His tag, which can be cleaved with thrombin.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the constructs provided by the invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of commercially-available prokaryotic expression vectors, and is useful for amplifying the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as dCK or a modified species of dCK polypeptide. As a result, increased quantities of a polypeptide such as dCK or a modified dCK polypeptide species are synthesized from the amplified DNA.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors comprising the recombinant expression constructs of the invention will typically contain a promoter that is recognized by the host organism and operably linked to the molecule encoding dCK or a modified dCK polypeptide species. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe genes to which they are operably linked, that is, with little or no control over gene expression. A large number of promoters, recognized by a variety of potential host cells, are well known. A suitable promoter is operably linked to the DNA encoding heavy chain or light chain comprising dCK or a modified dCK polypeptide of the invention by removing the promoter from the source DNA by restriction enzyme digestion and inserting the desired promoter sequence into the vector.

Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-10); CMV promoter (Thomsen et al., 1984, *Proc. Natl. Acad. USA* 81:659-663); the promoter contained in the 3' long terminal repeat of Rous sarcoma virus (Yamamoto, et al., 1980, *Cell* 22:787-97); herpes thymidine kinase promoter (Wagner et al., 1981, *Proc. Natl. Acad. Sci. U.S.A.* 78:1444-45); promoter and regulatory sequences from the metallothionine gene (Brinster et al., 1982, *Nature* 296:39-42); and prokaryotic promoters such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region that is active in pancreatic beta cells (Hanahan, 1985, *Nature* 315:115-22); the immunoglobulin gene control region that is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region that is active in testicular, breast, lymphoid and mast cells (Leder et al., 1986, *Cell* 45:485-95); the albumin gene control region that is active in liver (Pinkert et al., 1987, *Genes and Devel.* 1:268-76); the alpha-feto-protein gene control region that is active in liver (Krumlauf et al., 1985, *Mol. Cell. Biol.*, 5:1639-48; Hammer et al., 1987, *Science* 235:53-58); the alpha 1-antitrypsin gene control region that is active in liver (Kelsey et al., 1987, *Genes and Devel.* 1:161-71); the beta-globin gene control region that is active in myeloid cells (Mogram et al., 1985, *Nature* 315:338-40; Kollias et al., 1986, *Cell* 46:89-94); the myelin basic protein gene control region that is active in oligodendrocyte cells in the brain (Readhead et al., 1987, *Cell* 48:703-12); the myosin light chain-2 gene control region that is active in skeletal muscle (Sani, 1985, *Nature* 314:283-86); and the gonadotropic releasing hormone gene control region that is active in the hypothalamus (Mason et al., 1986, *Science* 234:1372-78).

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

An enhancer sequence may be inserted into the vector to increase transcription of DNA encoding dCK or a modified dCK polypeptide of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

A sequence encoding an appropriate native or heterologous signal sequence (leader sequence or signal peptide) can be incorporated into an expression vector, to promote extracellular secretion of the polypeptide. The choice of signal peptide or leader depends on the type of host cells in which the polypeptide is produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al. (1984, *Nature* 312: 768); the interleukin-4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846.

Recombinant expression constructs of the invention may be produced from a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the recombinant expression construct has be produced and a nucleic acid molecule encoding a dCK or a modified dCK polypeptide has been inserted into the proper site of the vector, the completed construct is advantageously inserted into a suitable host cell for amplification and/or polypeptide expression. The transformation of an expression vector for a dCK or a modified dCK polypeptide into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

A host cell, when cultured under appropriate conditions, will synthesize dCK or a modified dCK polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. In addition, dCK can be expressed in a bacterial expression system using, for example, BL21(DE3) competent cells.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produced a dCK or a modified dCK polypeptide. In another embodiment, a cell line from the B cell lineage that does not make its own antibody but has a capacity to make and secrete a heterologous antibody can be selected.

In some embodiments, the invention provides pharmaceutical compositions comprising a therapeutically effective amount of one or a plurality of the antibody-enzyme conjugates of the invention together with a pharmaceutically acceptable diluent, carrier, solubilizer, emulsifier, preservative, and/or adjuvant. Preferably, acceptable formulation materials are nontoxic to recipients at the dosages and concentrations employed. In preferred embodiments, pharmaceutical compositions comprising a therapeutically effective amount of a modified dCK polypeptide or an antibody-conjugated enzyme of the invention are provided.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18$^{th}$ Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, pharmaceutical compositions, antibody-conjugated enzymes, and/or modified enzymes of the invention, may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, dCK or modified dCK polypeptide or an antibody-conjugated enzyme of the invention may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired modified dCK polypeptide or an antibody-conjugated enzyme of the invention in a pharmaceutically acceptable vehicle. A particularly suitable vehicle for parenteral injection is sterile distilled water in which the modified dCK polypeptide or an antibody-conjugated enzyme of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, modified dCK polypeptide or an antibody-conjugated enzyme of the invention are advantageously formulated as a dry, inhalable powder. In preferred embodiments, modified dCK polypeptide or antibody-conjugated enzyme inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Modified dCK polypeptides or antibody-conjugated enzymes of the invention that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the modified dCK polypeptide or an antibody-conjugated enzyme of the invention. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of modified dCK polypeptides or antibody-conjugated enzymes of the invention in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving modified dCK polypeptides or antibody-conjugated enzymes of the invention in sustained- or controlled-delivery formulations. Techniques for formulating a variety of other sustained- or controlled-delivery means, such as liposome carriers, bioerodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 22:547-556), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of a modified dCK polypeptide- or an antibody-conjugated enzyme of the invention-containing pharmaceutical composition to be employed will depend, for example, upon the therapeutic context and objectives. One skilled in the art will appreciate that the appropriate dosage levels for treatment will vary depending, in part, upon the molecule delivered, the indication for which the modified dCK polypeptide or an antibody-conjugated enzyme of the invention is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In preferred embodiments, the dosage may range from 0.1 µg/kg up to about 30 mg/kg, optionally from 1 µg/kg up to about 30 mg/kg or from 10 µg/kg up to about 5 mg/kg.

Dosing frequency will depend upon the pharmacokinetic parameters of the particular modified dCK polypeptide or antibody-conjugated enzyme of the invention in the formulation used. Typically, a clinician administers the composition until a dosage is reached that achieves the desired effect. The composition may therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antibodies of the invention can be administered to patients throughout an extended time period. Chronic administration of an antibody of the invention minimizes the adverse immune or allergic response commonly associated with antibodies that are raised against a human antigen in a non-human animal, for example, a non-fully human antibody or non-human antibody produced in a non-human species.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use pharmaceutical compositions of the invention according to the invention ex vivo. In such instances, cells, tissues or organs that have been removed from the patient are exposed to pharmaceutical compositions of the invention after which the cells, tissues and/or organs are subsequently implanted back into the patient.

In particular, modified dCK polypeptides or antibody-conjugated enzymes of the invention can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

The Examples, which follow, are illustrative of specific embodiments of the invention, and various uses thereof. They are set forth for explanatory purposes only, and are not to be taken as limiting the invention.

EXAMPLES

Example 1

Cloning, Expression, Purification, and Crystallization of Human Deoxycytidine Kinase (dCK)

Human dCK was amplified from a cDNA library and cloned into the pET14b vector. Primer oligonucleotides were designed based on the published DNA sequence, introducing suitable endonuclease restriction sites at either end to facilitate direct cloning into the pET14b bacterial expression vector. Clone integrity was verified by automated DNA sequencing. BL21(DE3) *E. coli* carrying the recombinant plasmid coding for histidine-tagged dCK was grown in 2YT media at 37° C., induced with 0.1 mM isopropyl-beta-D-thiogalactopyranoside (IPTG) and harvested after 8 hours. The cell pellet was lysed by sonication, and loaded on a TALON $Co^{2+}$-affinity column (Clontech, Palo Alto, Calif.). After washing and elution with imidazole, the his-tag was cleaved by thrombin. The protein was further purified on an ion-exchange column and a gel filtration column (S-200). Selenomethionine-substituted protein was produced by following an established protocol (Doublie, 1997, *Methods Enzymol.* 276:523-30).

Crystals of human dCK in complex with nucleosides and nucleotides (dC and ADP, ara-C and ADP, gemcitabine and ADP) were grown by the vapor diffusion method using either the sitting-drop or the hanging-drop geometry. Nucleotides were from Sigma (St. Louis, Mo.) except for gemcitabine, which was a gift from Eli Lilly & Co (Indianapolis, Ind.). After formation of the respective complex by mixing dC (or ara-C or gemcitabine) together with ADP (final concentration of 5 mM each) and the dialyzed enzyme solution (12 mg $ml^{-1}$ dCK, 5 mM $MgCl_2$, 20 mM Hepes, pH 7.5, 5 mM DTT, 100 µM dC/ara-C/gemcitabine), 2 µl of the premixed solution were added to 2 µl of the reservoir solution and left to equilibrate at 20° C. against the reservoir. Tetragonal crystals were obtained from sitting-drops using a reservoir solution that contained 0.95-1.0 M citrate trisodium dihydrate and 100 mM Hepes, pH 7.5, or from hanging-drops using 20% (w/v) PEG1K, 100 mM magnesium acetate, and 100 mM Tris, pH 9.0. At times, the citrate condition also gave orthogonal crystals. Typically, crystals grew within one week to dimensions of 200×100×100 $µm^3$.

Crystals were transferred to a cryoprotectant solution that in the case of the citrate condition was made of mineral oil (Sigma) while for the crystals grown in PEG it was composed of the mother liquor and 10% (w/v) xylitol-10% (w/v) sucrose. Once the crystals were mounted in loops, they were frozen by directly immersing them in liquid nitrogen. X-ray data were collected at the Advanced Photon Source using the BioCARS beamlines BM-C and BM-D, and the SERCAT beamline ID-22. The data were indexed, scaled and merged using the programs XDS and XSCALE (Kabsch, 1993, *J. Appl. Crystal* 24:795-800) or Denzo and Scalepack (Otwinowski and Minor, 1997, *Methods Enzymol.* 276:307-326). Data collection statistics for all data sets are shown in Table 2.

TABLE 2

Data collection, phasing, and refinement statistics

| | MAD | | | dC-ADP | dC-ADP | ara-C-ADP-Mg | gemcitabine-ADP-Mg |
|---|---|---|---|---|---|---|---|
| *Data collection statistics* | | | | | | | |
| Beamline | | 14-BM-D | | 14-BM-C | 14-BM-C | 22-ID | 22-ID |
| Wavelength (Å) | 0.97997 | 0.97973 | 0.95705 | 0.9 | 0.9 | 1.0 | 1.0 |
| Temperature (K) | | 100 | | 100 | 100 | 100 | 100 |
| Resolution (Å) | | 2.3 | | 1.96 | 2.2 | 1.6 | 1.9 |
| Observed reflections | 257787 | 257933 | 258286 | 270973 | 219344 | 487680 | 326066 |
| Unique reflections | 24032 | 23928 | 24055 | 39237 | 15406 | 41313 | 27499 |
| Completeness (%, overall/last shell) | 94.5 (64.0) | 94.0 (61.8) | 94.6 (64.8) | 97.4 (67.8) (1.96-2.0 Å) | 95.9 (78.2) (2.2-2.3 Å) | 99.0 (99.6) (1.6-1.7 Å) | 99.5 (99.4) (1.9-1.95 Å) |
| Rsym (%, overall/last shell) | 4.5 (31.1) | 4.7 (32.1) | 4.6 (33.1) | 4.5 (29.1) | 6.4 (15.6) | 5.2 (51.1) | 5.4 (53.3) |
| I/σ(I) (overall/last shell) | 29.5 (3.3) | 27.8 (3.1) | 28.9 (2.8) | 23.7 (3.3) | 28.2 (7.5) | 23.1 (4.9) | 24.2 (4.7) |
| Space group | | $P4_32_12$ | | $C222_1$ | $P4_32_12$ | $P4_32_12$ | $P4_32_12$ |
| Unit cell (Å) | | | | | | | |
| a= | | 79.64 | | 52.74 | 80.00 | 80.72 | 80.20 |
| b= | | 79.64 | | 132.92 | 80.00 | 80.72 | 80.20 |
| c= | | 93.71 | | 157.64 | 93.95 | 94.28 | 94.60 |
| Molecules per au | | 1 | | 2 | 1 | 1 | 1 |
| *Phasing statistics* | | | | | | | |
| Heavy atom sites (Se) | | 4 | | | | | |
| Figure of Merit | | 0.54 | | | | | |
| *Refinement statistics* | | | | | | | |
| $R_{factor}/R_{free}$ (%) | | | | 16.1/20.3 | 22.1/28.0 | 17.3/19.7 | 17.9/20.7 |
| Resolution range (Å) | | | | 20-1.96 | 20-2.2 | 20-1.6 | 20-1.9 |

TABLE 2-continued

Data collection, phasing, and refinement statistics

| | MAD | dC-ADP | dC-ADP | ara-C-ADP-Mg | gemcitabine-ADP-Mg |
|---|---|---|---|---|---|
| No. of atoms/molecules | | | | | |
| protein | | (A) 1990 (B) 1830 | 1869 | 1982 | 1892 |
| nucleoside | | 16 × 2 | 16 | 17 | 18 |
| ADP | | 27 × 2 | 27 | 27 | 27 |
| waters | | 333 | 131 | 173 | 141 |
| R.m.s. deviation | | | | | |
| bond length (Å) | | 0.020 | 0.021 | 0.018 | 0.021 |
| bond angles (Å) | | 1.922 | 1.885 | 1.770 | 1.966 |
| Average B-factor (Å$^2$) | | | | | |
| protein (main chain) | | (A) 27 (B) 28 | 43 | 27 | 34 |
| protein (side chain) | | (A) 29 (B) 31 | 44 | 30 | 37 |
| ADP | | (A) 22 (B) 23 | 37 | 22 | 30 |
| nucleoside | | (A) 20 (B) 22 | 33 | 20 | 26 |
| waters | | 37 | 47 | 37 | 41 |

Structure Determination and Refinement

The structure of human dCK was solved using the Multiwavelength Anomalous Dispersion (MAD) method (Hendrickson and Ogata, 1997, *Methods Enzymol.* 276:494-523). Using data from the inflection, the peak, and the remote wavelengths, 4 selenium atoms were located using SOLVE (Terwilliger, 1999, *Acta Cryst.* D55:1863-1871), The map calculated from the experimental phases allowed us to build a model of dCK in O (Jones et al., 1991, *Acta Cryst.* A47:110-119). Refinement was carried out using the programs CNS (Brünger, 1993, *X-PLOR: a system for X-ray crystallography and NMR*, Yale University Press, New Haven, Conn.) and REFMAC (Murshudov et al., 1997, *Acta Cryst.* D53:240-255). Data for the MAD data set were collected to 2.3 Å resolution. A partially built model into the MAD electron density was used to solve the tetragonal crystals. The electron density for dCK extended to the last residue (Leu260), while the N-terminus (residues 1 to 19) was flexible and could not be modelled. Deoxycytidine and ADP were modelled in the electron density map after most of the protein main chain and side chain atoms were built and refined. The ligands were refined without conformational torsion-angle restraints in order to prevent bias towards a particular ring conformation for the sugars. The final model of the complex of dCK with dC and ADP was used as starting model for the refinement of the other structures in the tetragonal space group, and to solve the structure of dCK that crystallized in the orthorhombic space group using AMoRe molecular replacement (Navaza, 1994, *Acta Cryst.* A50: 157-163).

Data for the ara-C-ADP•Mg and the gemcitabine-ADP•Mg complexes were collected to 1.6 Å and 1.9 Å resolution, respectively, on the crystals grown in PEG. Calculation of difference maps clearly showed the presence of substituents on the second position of the deoxyribose moiety of dC: an ara hydroxyl group in the case of ara-C, and two fluorine atoms in the case of gemcitabine. The ligands were modelled into the electron density maps after simulated annealing and refinement of the protein model. Water molecules were then automatically added using Arp/wARP (Perrakis et al., 1999, *Nat. Struct. Biol.* 6:458-63).

Analysis of Structural Information of Human dCK

The structural information of human dCK provided a tool to understand the enzyme's substrate specificity and has great potential for the contribution to the development of improved therapeutic agents that depend on dCK for activation.

Human dCK (FIGS. 2A and 2B) consists of 260 amino acid residues with a calculated molecular weight of 30.5 kDa. We solved the structure using the multiwavelength anomalous diffraction (MAD) method (Hendrickson and Ogata, 1997, *Methods Enzymol.* 276:494-523) on selenomethionine-containing protein. It is a homodimeric globular protein with a fold similar to that described for the *Drosophila melanogaster* nucleoside kinase (dNK) and human dGK (Johansson et al., 2001, *Nat. Struct. Biol.* 8:616-20). Each monomer has a five-stranded parallel β-sheet core surrounded by ten α helices. Helix α4 and α7 from each monomer create a four-helix bundle dimer interface.

In humans, four spatially segregated enzymes accomplish the first step in the salvage pathway of deoxyribonucleoside triphosphate synthesis. The mitochondrial kinases dGK and thymidine kinase 2 (TK2) supply the precursors for mitochondrial DNA synthesis, and dCK and thymidine kinase 1 (TK1) do the same for nuclear DNA. Since ultimately dCK and TK1 must provide all four DNA triphosphates, it is not surprising that dCK, in addition to phosphorylating deoxycytidine (dC), also efficiently phosphorylates deoxyguanosine (dG) and deoxyadenosine (dA). In fact, apart from the thymidine-specific TK1, deoxyribonucleoside kinases are characterized by their ability to phosphorylate substrates of different base constituents. Notably, dNK, the only deoxyribonucleoside kinase in *Drosophila*, phosphorylates all four physiological deoxyribonucleosides (Knecht et al., 2002, *EMBO J.* 21:1873-1880).

Figure 2:
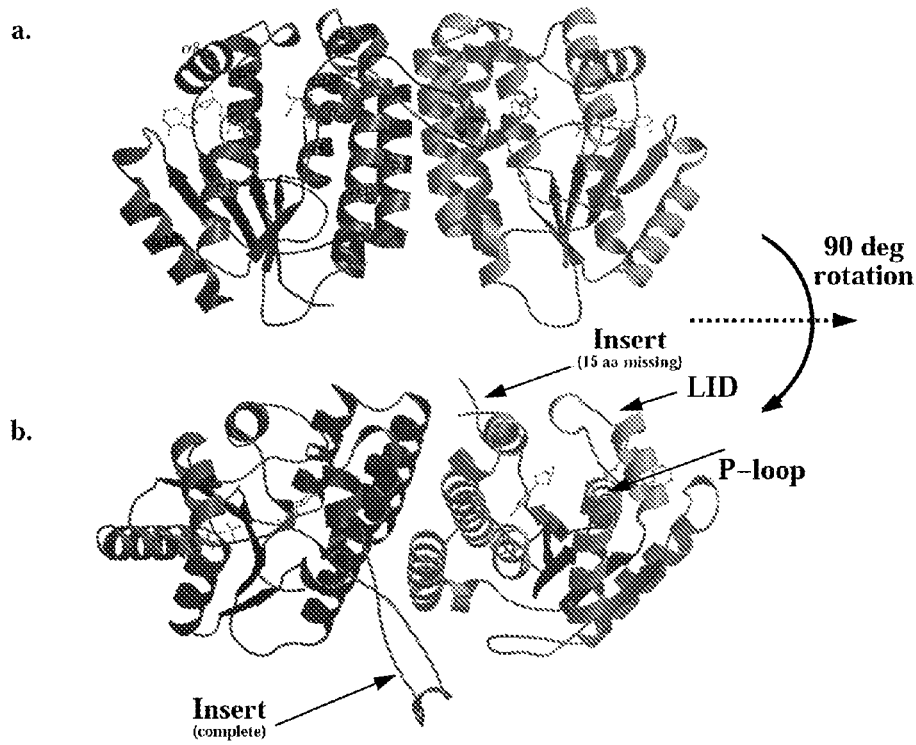
FIG. 2A is a ribbon diagram of human deoxycytidine kinase (dCK), a dimeric protein, in the presence of deoxycytosine (dC) and ADP. Human dCK contains a 15-residue long insert of unknown function (Ser63 to Asn77) between helix α2 and helix α3. A similar insert (12 residues long) is also present in human dGK (residues Ala80 to Ser91), but not in *Drosophila* dNK nor in human mitochondrial thymidine kinase (TK2).
FIG. 2B shows another view of the structure of human dCK in the presence of dC and ADP, rotated through 90 degrees from the view shown in FIG. 2A; the dashed arrow is the axis of rotation. The root mean square distance (r.m.s.d.) between Cα atoms of dCK and dGK or dNK is 1.17 Å, over 175 Cα. atoms, and 1.20 Å over 178 atoms, respectively.
FIG. 2C shows a sequence alignment of human dCK (SEQ ID NO: 1), human dGK (SEQ ID NO: 2), *Drosophila* dNK (SEQ ID NO: 3) and human mitochondrial TK2 (SEQ ID NO: 4).
Figure 2:
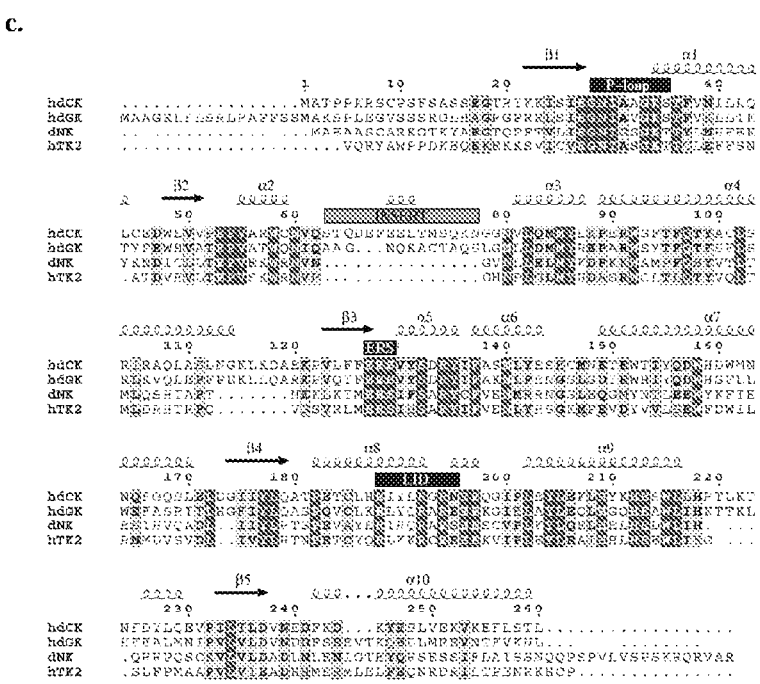
Figure 3:
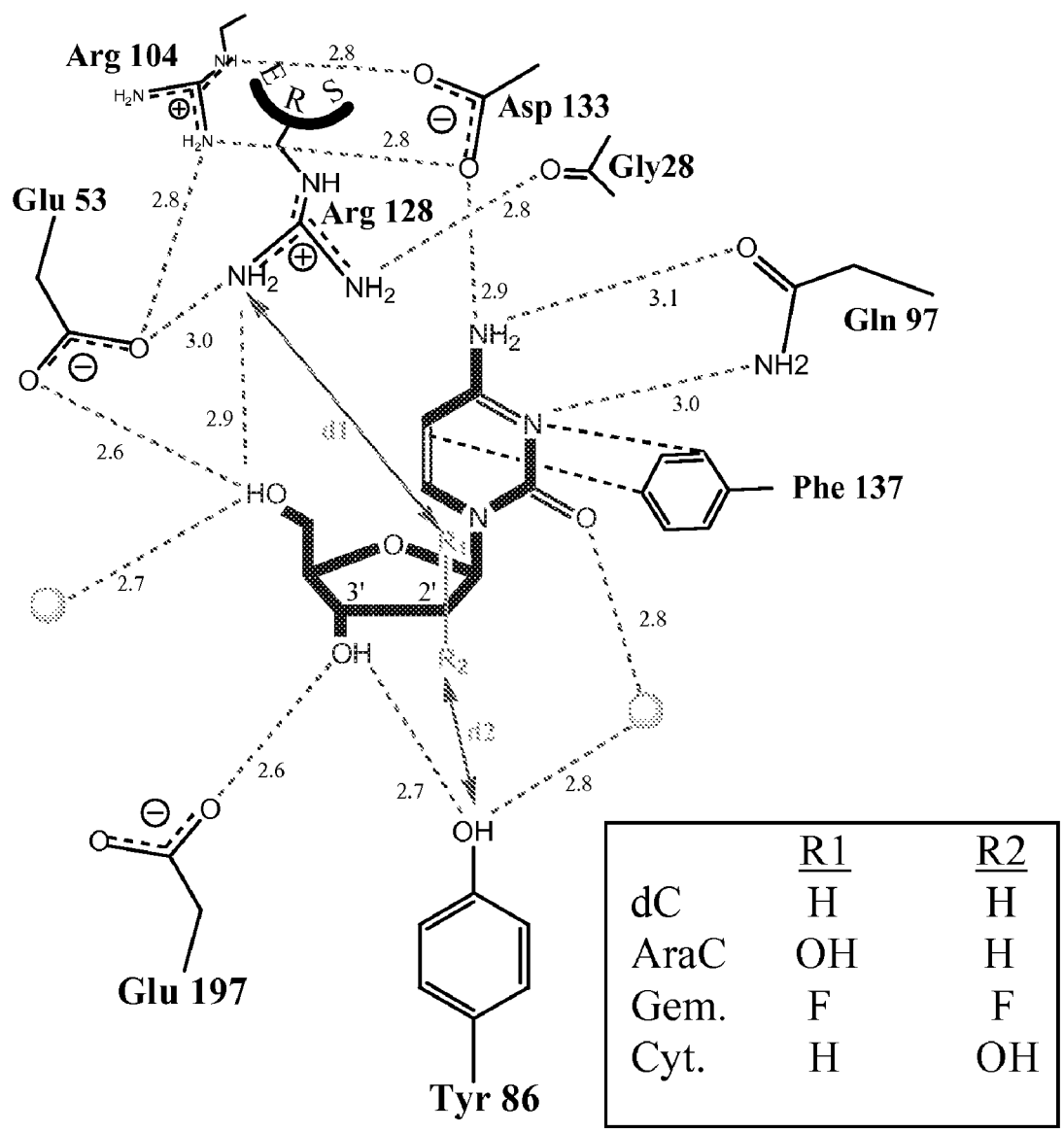
FIG. 3 is a schematic representation of the interactions made by the bound nucleoside with dCK. Arg128 of the enzyme reactive site (ERS) motif interacts with the putative base, Glu53, which is proposed to accept the proton from the substrate's 5'-hydroxyl, and with the 2'-arabinosyl ($R_1$) substituent in ara-C (a OH) or in gemcitabine (a fluorine). In the case of gemcitabine, an additional interaction is possible between the 2'-ribosyl ($R_2$) fluorine atom and Tyr86. Interactions present only with the prodrugs are labeled as d1 and d2. All distances are in angstroms.

The ability of dCK to accommodate multiple substrates that are of opposite hydrogen bonding character was due to the conserved Gln97 (FIG. 2C). The hydrogen bond donating and accepting moieties of the glutamine side chain rotated and positioned themselves according to the nature of the base bound. In the structures with cytosine nucleosides, the side chain of Gln97 acted as a hydrogen bond donor, via its amide group, to the cytosine N3 atom, and as a hydrogen bond acceptor, via the carbonyl group, to the cytosine amino group (FIG. 3). This cytosine amino group also interacted with the side chain of Asp133. Discrimination by dCK against the pyrimidines thymidine and deoxyuridine was achieved because of the inability of Asp133 to perform favorable hydrogen bonding interactions in the case of a thymine or uracil base.

Adding to the discrimination against thymidine (but not deoxyuridine) is a predicted steric clash between Arg104 and the thymine methyl group. Support of this interpretation comes from mutation experiments on dNK done by Knecht et al. (2002, *EMBO J.* 21:1873-1880) and from kinetic results with a dCK triple mutant we designed. In this mutant, the discriminating residues Arg104 and Asp133 were changed to a methionine and an alanine, respectively, and, as a consequence, the dCK mutant gained the ability to phosphorylate thymidine. Further interactions made between the cytosine base and dCK included a hydrophobic interaction to Phe137, and a hydrogen bond to a water molecule that bridged the base and Tyr86. The interaction with Tyr86 effected deoxyribose- versus ribonucleosides discrimination.

Figure 4:
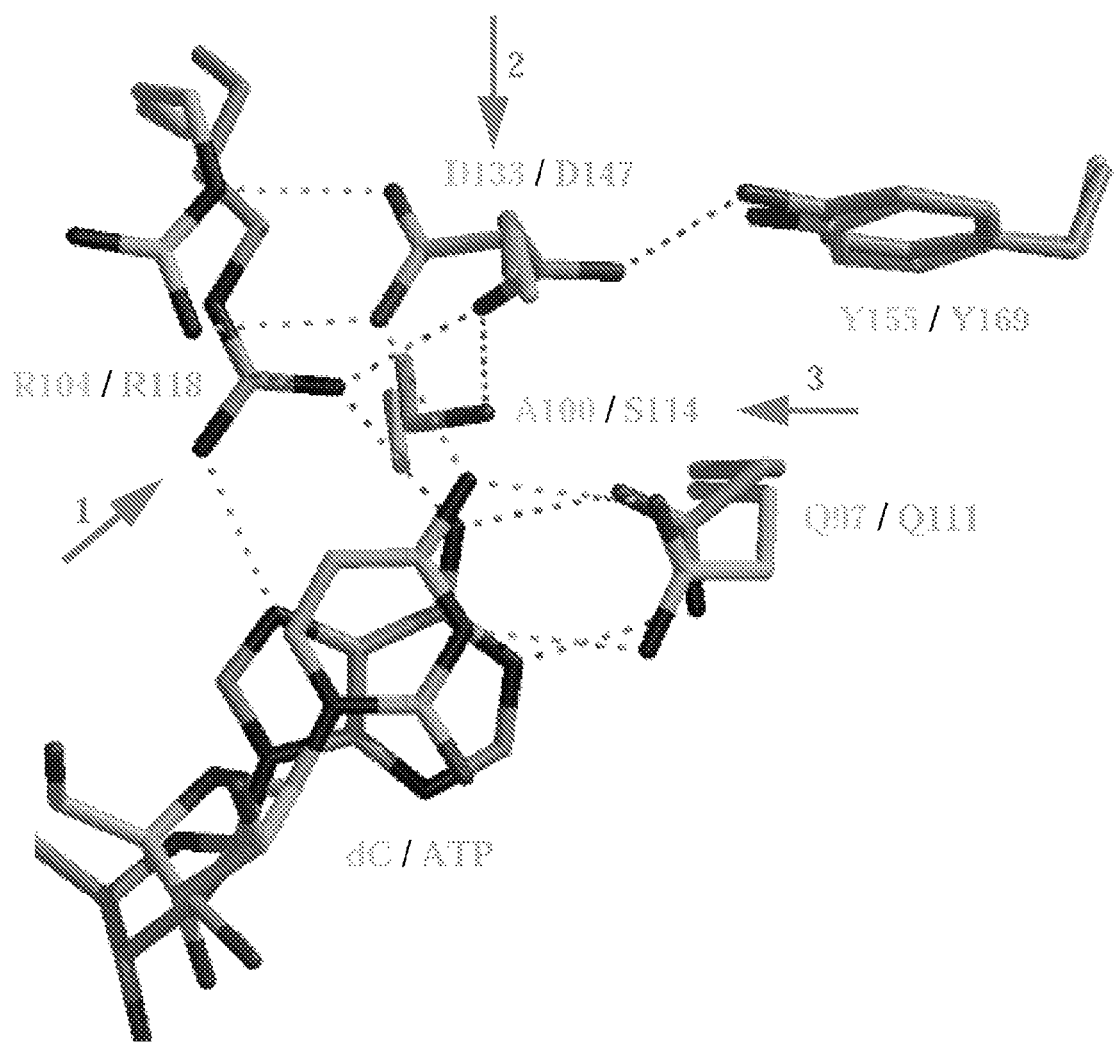
FIG. 4 shows superposition of dCK- and dGK-active site residues.

While both dCK and dGK phosphorylate dA and dG, only dCK is capable of phosphorylating dC and its analogs such as ara-C (Herrstrom et al., 1998, *Mol. Pharmacol.* 53:270-273). The structures of dCK with dC revealed that in order to accommodate dC, Arg104 assumed a different conformation to that of Arg118 observed in the structure of dGK (FIG. 4, arrow 1). An aspartic acid residue in both the dCK and dGK structures interacted with the above-mentioned arginine (FIG. 4, arrow 2). However, only in dGK was a serine at position 114 able to participate in this network, adding to its stabilization. In contrast, in dCK at the position of the dGK-Ser114 was an alanine residue (FIG. 4, arrow 3). By having an alanine instead of a serine, the hydrogen-bonding network holding rigid the aspartic acid and arginine residues was weaker, allowing for a less extended conformation of Arg104 with a concomitant change in conformation for Asp133 upon dC binding. At the same time, upon purine binding to dCK, a change in the Arg104 to an extended conformation as observed in the dGK structure was still possible. The conserved tyrosine in position 155 supplied an important hydrogen bond to Asp133 in the conformation compatible with purine binding.

A common feature among the nucleoside kinases is the stabilization of the sugar 3'-hydroxyl group by a conserved Tyr-Glu pair (dCK-$Y_{86}E_{197}$; dGK-$Y_{100}E_{211}$; dNK-$Y_{70}L_{172}$) (Johansson et al., 2001, *Nat. Struct. Biol.* 8:616-20). Due to proximity of the tyrosine hydroxyl group to the 2'-sugar position, this residue functions to favor deoxyribonucleosides over ribonucleosides. The isosteric substitutions of protons by fluorines at the 2'-position in gemcitabine put one of these fluorines at an interacting distance to the tyrosine hydroxyl group. Even a slightly larger substituent at this position resulted in some steric repulsion, as evidenced by the high $K_M$ of cytidine in comparison to that of deoxycytidine (Table 2).

Figure 5:
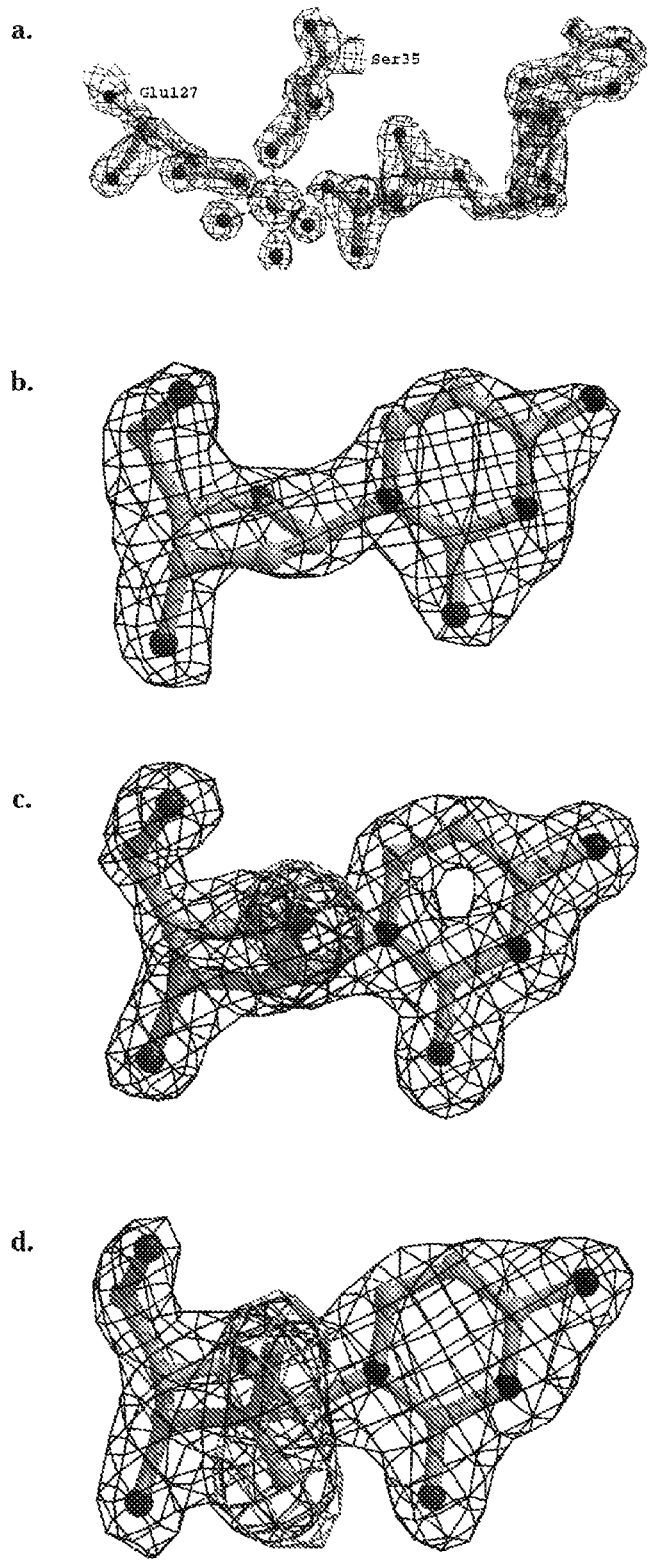
FIG. 5A shows an electron density map of dCK bound to an ADP molecule with an octahedral coordinated magnesium atom.
FIG. 5B shows an electron density map of dCK bound to deoxycytidine.
FIG. 5C shows an electron density map of dCK bound to AraC.
FIG. 5D shows an electron density map of dCK bound to gemcitabine.

The structures of dCK with ara-C-ADP•Mg and the one with gemcitabine-ADP•Mg (FIG. 5) were both similar to the dC-ADP complex, with a root mean square deviation of 0.66 Å and 0.63 Å, respectively. Compared to the structure with dC bound in the active site, the hydroxyl group in the 2'-position of the arabinofuranosyl sugar in ara-C provided an additional 3.0 Å (d1, FIG. 3) hydrogen bond to the conserved Arg128 of the ERS motif (FIG. 2C). A similar interaction (2.9 Å) with Arg128 was formed by the fluorine atom ($R_1$) of gemcitabine, while the other fluorine ($R_2$) made a 2.7 Å hydrogen bond with Tyr86 (d2, FIG. 3).

The proton from the sugar 5'-hydroxyl could be accepted by a nearby base (either prior to the O5' nucleophilic attack on the ATP γ-phosphate, or after the formation of the O—P bond). The conserved Glu53 at hydrogen bonding distance to the sugar 5'-hydroxyl group (2.6 Å via OE2) and to NH1 of Arg128 (3.0 Å via OE1) (FIG. 3) was a very likely candidate for the fulfillment of this role as base. In the three complexes, the atomic positions of Glu53, Arg128 and the nucleoside/ prodrugs were identical within experimental error, suggesting that the origin of the increased dCK activity towards the two cytosine analogs resulted from the interactions of Arg128 to R1 and of Tyr86 to R2.

Both ara-C and gemcitabine possess the Arg128 to R1 interaction and the increase in enzymatic efficiency for the two prodrugs was similar demonstrating that this interaction plays a predominant role. Assuming that the observed steady-state kinetic rate reflected the phosphoryl transfer step, then the increased rate for ara-C/gemcitabine could be explained as follows: in the presence of dC, the interaction between Glu53 and Arg128 was not weakened by the substrate. However, a hydrogen-bond acceptor at the 2'-arabinosyl position, as present in ara-C and gemcitabine, competed with Glu53 for the Arg128 interaction. A weaker Glu53-Arg128 interaction would potentiate the proton accepting ability of the carboxylic acid group from the O5'-hydroxyl. As a result, the nucleoside 5'-hydroxyl group would become more nucleophilic and hence the $k_{cat}$ for ara-C and gemcitabine phosphorylation was increased.

The positive influence of hydrogen-bonding acceptor substituents at the 2'-arabinosyl position on dCK activity was also supported by the recent discovery that the purine drug 2-chloro-2'-arabino-fluoro-2'-deoxyadenosine, clofarabine, a new derivative of cladribine that is currently undergoing phase II clinical trial for pediatric leukemia, is ~3-fold more efficient substrate for dCK than cladribine (Lotfi et al., 1999, *Clin. Cancer Res.* 5:2438-44; Mansson et al., 2003, *Biochem. Pharmacol.* 65:237-247). On the basis of the structures presented here, this improvement was likely caused by the interaction of the 2'-arabino-fluorine atom of clofarabine with Arg128, thus improving the ability of Glu53 to function as a base.

Another important interaction involved in the stabilization and positioning of the nucleoside sugar was made by the 3'-hydroxyl group. The complexes with ara-C and gemcitabine were crystallized under the same conditions as that of dC. However, with the antiviral drug 2',3'-dideoxy-cytidine (ddC) no crystals were obtained. This may suggest that weak ddC binding ($K_M$ of 407 µM versus 6.2 µM for dC, Table 2) did not induce the same enzyme conformation necessary to promote crystal growth. A likely explanation for such behavior could be found in the lack of the 3'-hydroxyl group in ddC. Indeed, in all the dC, ara-C and gemcitabine structures, the 3'-hydroxyl group was held in place by Glu197 and Tyr86 (FIG. 3), which are strictly conserved residues within the deoxyribonucleoside kinases dCK, dGK, TK2 and dNK (FIG. 2C).

Thus, modified prodrug molecules that include a hydrogen bond acceptor(s) at the 2'-position (e.g. hydroxyl group or fluorine in the 2'-arabinosyl position, or fluorines in both 2'-positions) would counter the low phosphorylation efficiency of ddC, and hence increase its antiviral effect.

Improving dCK Catalytic Efficiency dCK is an inefficient enzyme as a result of a very slow $k_{cat}$ (0.03 sec$^{-1}$; Table 2). In contrast, dNK exhibits a 2,500-fold higher efficiency for dC phosphorylation resulting mainly from its faster $k_{cat}$ (16.5 sec$^{-1}$) (Knecht et al., 2002, *EMBO J.* 21:1873-1880). With the goal of making dCK more active key active site residues in dCK were mutated to those found in dNK. First, the structures of human dCK and the *drosophila* dNK were overlayed. This permitted residues likely to be important for catalysis to be identified. It was expected that residues present in dNK but absent in dCK and identified in this manner would also identify residues involved in or responsible for dNK's higher enzymatic rate. Since Arg104 plays a role in the already mentioned active site hydrogen-bonding network, its mutation to the uncharged methionine was combined with the compensatory change of Asp133 to an alanine. The resulting double mutant has an amino acid sequence as set forth in SEQ ID NO:6. In addition, Ala100 was changed to a valine as is found in dNK.

Steady-state kinetic assays were performed by determining deoxycytidine kinase activity using a calorimetric assay (Agarwal et al., 1978, *Methods Enzymol.* 51:483-490) in 50 mM Tris/HCl, pH 7.5, 100 mM KCl, 5 mM MgCl$_2$, at 37° C. The concentration of dCK was 0.4 µM, ATP•Mg 1 mM, while for the nucleosides and the nucleoside analogs a range of concentrations between 10 µM and 1 mM were used. All experiments were performed in duplicates.

The steady-state kinetic experiments using ara-C, gemcitabine and dC as substrates showed that there was a 10-fold increase in the $k_{cat}$ but only a slight increase in $K_M$ for the two prodrugs compared to dC (Table 3). Overall there was a ~4-fold higher enzymatic efficiency for dCK with ara-C and gemcitabine.

Table 3 demonstrates that the triple mutant A100V/R104M/D133A of human dCK was more active than wild-type enzyme.

TABLE 3

Steady State Kinetic Data

| Nucleoside | $K_M$ (µM) | $k_{cat}$ (sec$^{-1}$) | $k_{cat}/K_M$ (M$^{-1}$ sec$^{-1}$) |
|---|---|---|---|
| Wild Type dCK | | | |
| dC | 6.2 | 0.03 | 4.8 × 10$^3$ |
| ddC | 406.8 | 0.18 | 0.4 × 10$^3$ |
| cytidine | 382.7 | 0.74 | 1.9 × 10$^3$ |
| ara-C | 15.5 | 0.26 | 16.8 × 10$^3$ |
| gemcitabine | 22.0 | 0.37 | 16.8 × 10$^3$ |
| A100V/R104M/D133A-dCK | | | |
| dC | 4 | 0.93 | 232.5 × 10$^3$ |
| ara-C | 102 | 1.73 | 17.0 × 10$^3$ |
| gemcitabine | 50 | 3.52 | 70.4 × 10$^3$ |

The kinetic data for the dCK triple mutant A100V/R104M/D133A were encouraging: efficiency towards dC increased by 50-fold, towards gemcitabine by 4-fold, with no change for ara-C (Table 3).

In conclusion, the high-resolution structures of dCK in complex with dC and two clinically used prodrugs revealed determinants of substrate specificity. Moreover, the structures are useful as starting point for the design of superior nucleoside analogs, taking into account the structural constraints imposed by the dCK active site. Since in many cases it is the dCK phosphorylation step that limits the efficacy of clinically used prodrugs, more efficient prodrug phosphorylation by dCK is predicted to result in potentiated antiviral and anti-cancer response. Lastly, we have shown the use of the structure to design a dCK mutant of improved activity, as a first step towards the use of such an enzyme in suicide gene therapy applications.

Example 2

Conjugation of HuM195 to dCK

In-vitro purified dCK was chemically conjugated to HuM195 (Protein Design Laboratories, Fremont, Calif.). A purification protocol was used to obtain only the conjugate, which was performed as follows. A Sepharose S-200 column (Amersham Biosciences), a column that separate macromolecules according to size was used, wherein the first peak to elute for the column was the HuM195-dCK conjugate. Only this peak was collected, and concentrated to ~3 mg/ml. The activity of the conjugate was verified using a colormetric spectrophotometric assay. A standard protein conjugation technique was used for the conjugation of wild type dCK with HuM195. Conjugation of enzymes to antibodies involves a formation of a stable covalent linkage between an enzyme and an antigen specific monoclonal or polyclonal antibody in which neither the antigen-combining site of the antibody nor the active site of the enzyme is functionally altered. Briefly, the enzyme dCK was dialyzed against 2 liters of 0.1M phosphate buffer overnight at 4° C. while stirring gently. Afterward, the phosphate buffer was replaced and dialysis was continued for 2 hours. Then M-maleimido benzoyl N-hydroxy Succinimide Ester in dimethyl formamide (MBS/DMF) solution was added to the monoclonal antibody HuM195 (MBS/antibody ratio 120:1) and the mixture was stirred gently at room temperature for 30 minutes. The solution was then filtered and loaded on the Hi Prep 26/10 desalting column, which was pre-equilibrated with 100 ml phosphate buffer. The first peak was collected and concentrated into 1.5 ml; the second peak contained free MBS. The concentrated first peak was pooled with dialyzed enzyme (enzyme antibody weight ratio was 4:1) and stirred for 2 hours at room temperature. After 2 hours, the solution was filtered and injected into Superdex 200 gel filtration column. The first peak, which was the HuM195 TMPK conjugation product, was eluted and concentrated. A gel electrophoresis was then run and the conjugation product is confirmed.

HuM195-dCK activity was determined using a colorimetric assay in 50 mM Tris/HCl, pH7.5, 100 mM KCl, 5 mM MgCl2, at 37° C. The concentrations used were: HuM195-dCK 0.4 µM, ATP Mg 1 mM, and the nucleosides and nucleoside analogs in a range of concentrations between 10 µM and 1 mM. All experiments were performed in duplicate. Kinetic data were evaluated using the program Sigma Plot 2000 and were best described by the Michaelis-Menten equation v=Vmax X [S]/(Km+[S]).

Example 3

Testing the HuM195-dCK Conjugate in CD33 Positive Cell Lines

Figure 6:
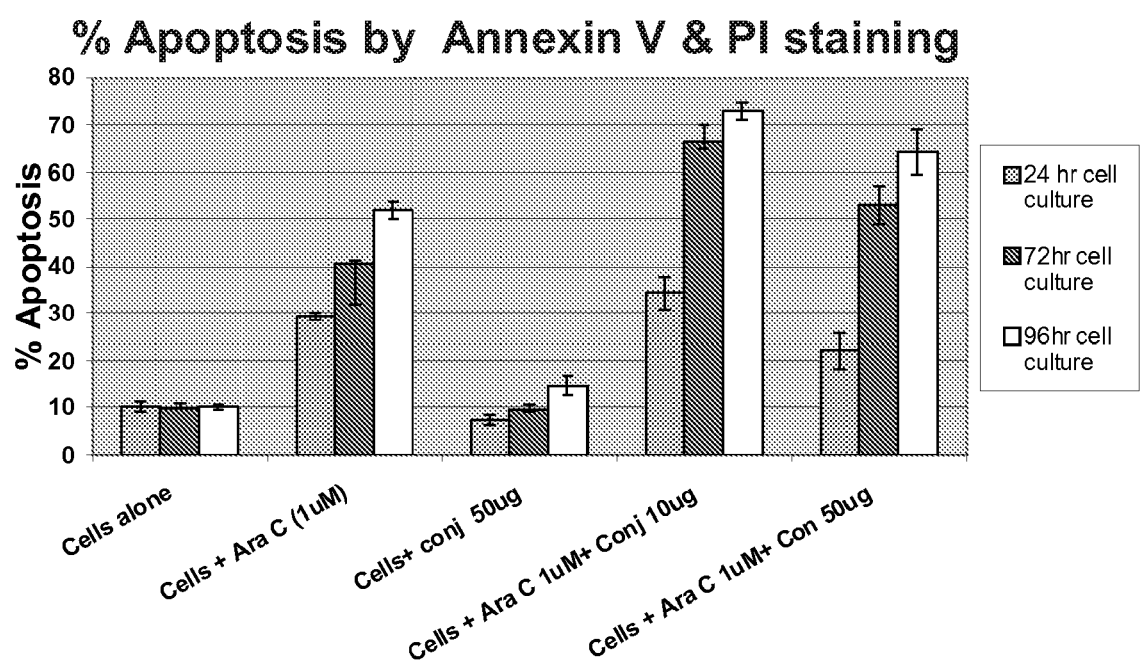
FIG. 6 depicts a graph demonstrating an increased percentage of apoptotic HL60 cells treated with AraC alone, the dCK-antibody conjugate alone, or in combination.

The HuM195 antibody will only bind and internalize to cells expressing CD33. Thus, the HL60 cell line (derived from AML cells) and the NB4 cell line, which are CD33 positive, were used to test the activity of the HuM195-dCK system in live cells. The cells were treated with AraC, the HuM195-dCK conjugate, or the combination of HuM195-dCK and the AraC. Annexin V and propidium iodide (PI) staining was used to identify apoptotic cells. As shown in FIG. 6, cells alone as a control had about 10% cell death, AraC at 1 μM increased cell death as a function of time, with 50% cell death after 96 hours, the conjugate by itself was not toxic, and the conjugate in combination of AraC results in the most efficient cell death (~70% killing after 96 hours).

Figure 7:
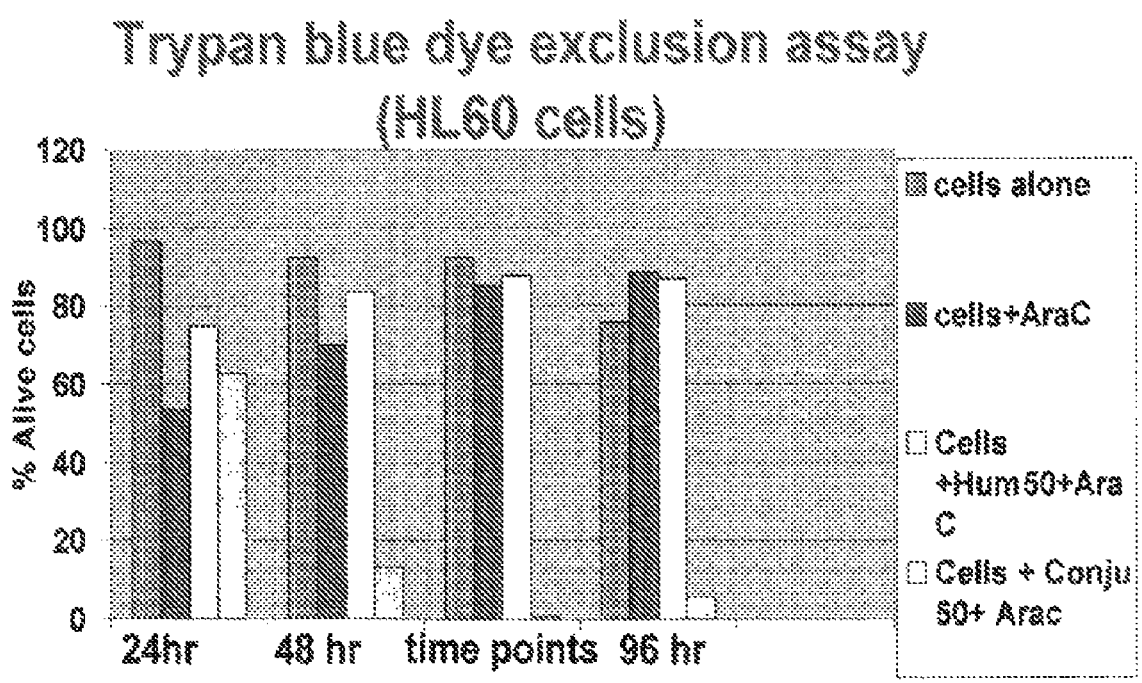
FIG. 7 depicts a graph demonstrating HL60 cell death assayed by trypan blue staining after treatment with AraC or dCK-antibody conjugate or in combination.

In addition, a trypan blue exclusion assay was performed on cells treated with AraC, the HuM195-dCK conjugate, or the combination of HuM195-dCK and the AraC (FIG. 7). In the trypan blue assay, a large number corresponds to a large number of living cells. As expected, the cells treated with a combination of the conjugate and AraC showed the most effective cell killing.

Figure 8:
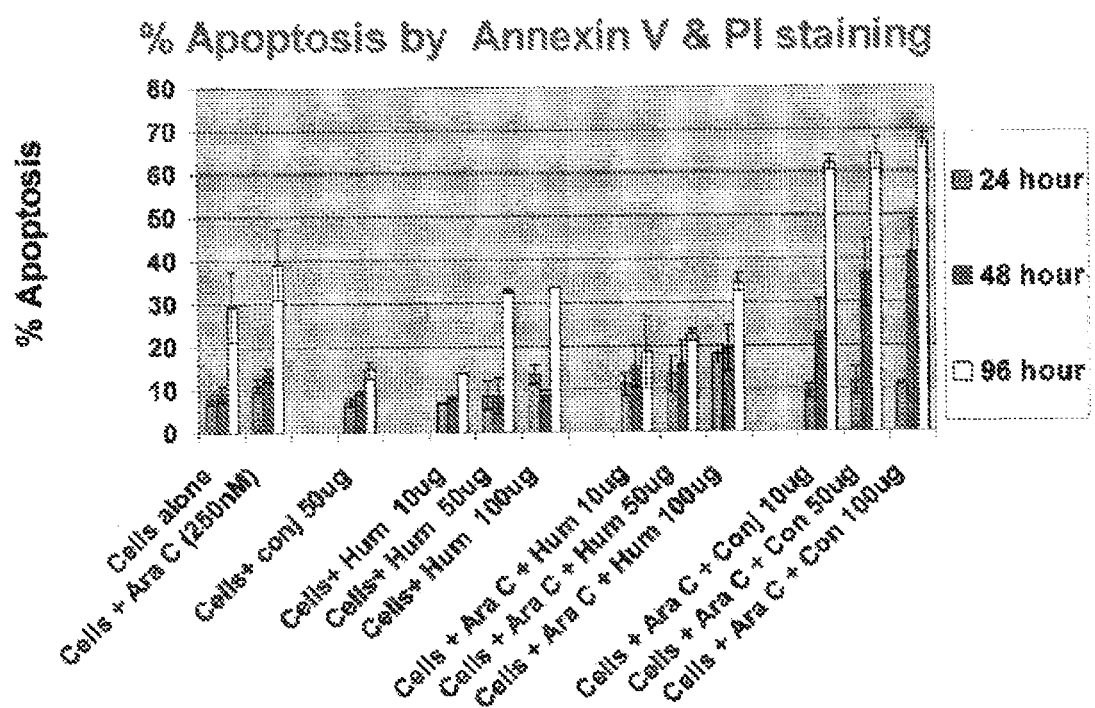
FIG. 8 depicts a graph demonstrating an increased percentage of apoptotic NB4 cells treated with AraC or the dCK-antibody conjugate or in combination.

The NB4 cells were also treated with AraC, the HuM195-dCK conjugate, or the combination of HuM195-dCK and the AraC, and an apoptosis assay was performed as above. The AraC dose used, however, was decreased from 1000 nM to 250 nM. The results were similar to those observed in the HL60 cells (FIG. 8). The conjugate with AraC (right bars) achieve ~65% cell killing after 96 hours, whereas AraC alone was below 40%.

Example 4

Verifying Specificity for CD33 Positive Cells

Figure 9A:
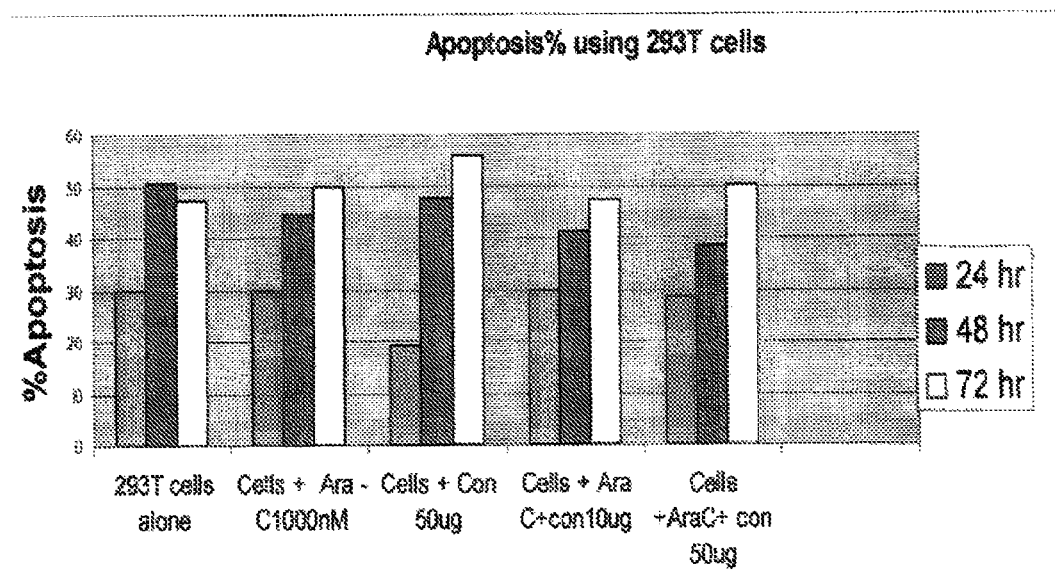
FIG. 9A depicts a graph demonstrating the percentage of apoptotic 293T cells treated with AraC or the dCK-antibody conjugate or in combination.
Figure 9B:
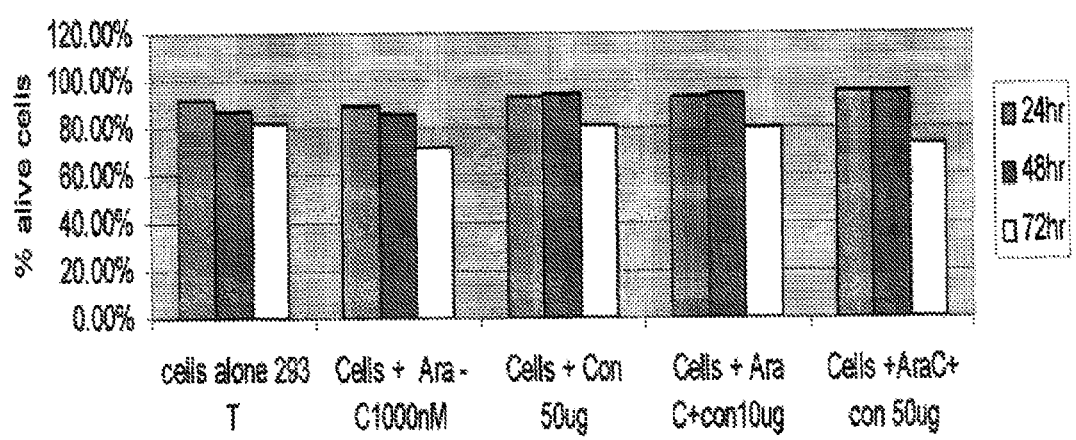
FIG. 9B depicts a graph demonstrating 293T cell death after treatment with AraC or the dCK-antibody conjugate or in combination.

To verify that the HuM195-dCK conjugate was only delivered to CD33 positive cells, experiments were repeated with CD33 negative cells (293T cells). Flow cytometry (FIG. 9A) and a trypan blue exclusion assay (FIG. 9B) were used to determine AraC-mediated cell killing. In both assays, similar killing efficiency for AraC and for the combination of AraC and the conjugate was observed. Thus, the conjugate did not enter the 293T cells as expected.

Example 5

Verifying Activity in Mouse Models of Leukemia

To verify the activity of the HuM195-dCK conjugate in mammals, C.B-17-SCID/SCID mice are used. The mice are irradiated with 300 cGY total body irradiation and after 2-4 hours of observation are injected intravenously via tail vein with $1 \times 10^7$ HL60 cells diluted in 0.1 ml of HBSS. A total of 20 control mice are used and the treated mice are injected intraperitoneally as follows: Group A: No treatment; Group B: Ara-C 1.0 μg/day (n=10); Group C: Ara-C 1.0 μg/day as well as the conjugate at varying doses of 10 and 50 μg/day (n=10 each); and Group D: conjugate alone 10 and 50 μg/day (n=10 each).

Group A is the control animals without any treatment. Group B reveals the therapeutic effect of Ara-C alone. Group D tests for the effect of the conjugate. Group C shows the synergistic effect of adding the conjugate to the Ara-C.

The mice are examined daily for overall activity and for presence of masses. Moribund mice are sacrificed. Samples from various mouse organs are removed and the tissues are fixed in formaldehyde embedded in paraffin and are examined under microscope. The median survival of the control mice is compared with the mice treated with Ara-C alone, Ara-C and conjugate and conjugate alone. Mice living more than 150 days are sacrificed and examined at autopsy for evidence of any HL60 related tumors in various organs including their bone marrow.

It should be understood that the foregoing disclosure emphasizes certain specific embodiments of the invention and that all modifications or alternatives equivalent thereto are within the spirit and scope of the invention as set forth in the appended claims.

What is claimed is:

1. A modified human deoxycytidine kinase having the amino acid sequence identified by SEQ ID NO: 1, wherein amino acid residue 104 and amino acid residue 133 are substituted, and wherein the modified human deoxycytidine kinase is capable of phosphorylating wild type human deoxycytidine kinase substrates.

2. The modified human deoxycytidine kinase of claim 1, wherein amino acid residue 104 is substituted with methionine.

3. The modified human deoxycytidine kinase of claim 1, wherein amino acid residue 133 is substituted with alanine.

4. The modified human deoxycytidine kinase of claim 1, wherein amino acid residue 104 is substituted with methionine, and amino acid residue 133 is substituted with alanine, and wherein the modified human deoxycytidine kinase has the amino acid sequence as identified by SEQ ID NO: 6.

5. The modified human deoxycytidine kinase of claim 1 wherein said modified human deoxycytidine kinase additionally phosphorylates thymidine or thymidine analogs.

6. A pharmaceutical composition comprising the modified human deoxycytidine kinase of claim 1 and a pharmaceutical acceptable carrier.

7. A pharmaceutical composition comprising the modified human deoxycytidine kinase of claim 2 and a pharmaceutically acceptable carrier.

8. A pharmaceutical composition comprising the modified human deoxycytidine kinase of claim 3 and a pharmaceutically acceptable carrier.

9. A pharmaceutical composition comprising the modified human deoxycytidine kinase of claim 4 and a pharmaceutically acceptable carrier.

* * * * *